United States Patent [19]

Arand et al.

[11] Patent Number: 5,613,496
[45] Date of Patent: Mar. 25, 1997

[54] METHOD AND APPARATUS FOR CREATING A REPRESENTATIVE HEARTBEAT FROM AN ECG WAVEFORM

[75] Inventors: Patricia A. Arand; William L. Post, both of McMinnville, Oreg.; Alfred D. Forbes, Palo Alto, Calif.

[73] Assignee: Hewlett-Packard Company, Palo Alto, Calif.

[21] Appl. No.: 565,504

[22] Filed: Nov. 29, 1995

[51] Int. Cl.$^6$ ................................................ A61B 5/0452
[52] U.S. Cl. ........................................................... 128/702
[58] Field of Search ......................... 346/413.06; 128/696, 128/699, 202, 703, 708

[56] References Cited

U.S. PATENT DOCUMENTS

| | | | |
|---|---|---|---|
| 3,654,916 | 4/1972 | Neilson | 128/702 |
| 4,023,564 | 5/1977 | Valiquette et al. | 128/708 |
| 4,120,296 | 10/1978 | Prinz | 128/2.05 |
| 4,170,992 | 10/1979 | Dillman | 128/702 |
| 4,259,966 | 4/1981 | Cannon et al. | 128/706 |
| 4,364,397 | 12/1982 | Citron et al. | 128/710 |
| 4,404,974 | 9/1983 | Titus | 128/670 |
| 4,420,000 | 12/1983 | Bailey | 128/706 |
| 4,519,395 | 5/1985 | Hrushesky | 128/671 |
| 4,589,420 | 5/1986 | Adams et al. | 128/702 |
| 4,630,204 | 12/1986 | Mortara | 364/417 |
| 4,924,875 | 5/1990 | Chamoun | 128/702 |
| 5,284,152 | 2/1994 | Portnuff et al. | 128/710 |

OTHER PUBLICATIONS

"Influence Of Noise On Wave Boundary Recognition By ECG Measurement Programs", by J. L. Willems, Chr. Zywietz, P. Arnaud, J. H. Van Bemmel, R. Degani, and P. W. MacFarlane, Computers & Biomedical Research, 1987, pp. 543–562.

"Fast And Reliable QRS Alignment Technique For High-Frequency Analysis of Signal-Averaged ECG", by O. J. Escalona, R. H. Mitchell, D. E. Balderson, and D. W. G. Harron, MBEC Kyoto World Congress Supplement, Jul. 1993, pp. S137–S146.

*Primary Examiner*—William E. Kamm
*Attorney, Agent, or Firm*—Curtis G. Rose

[57] ABSTRACT

A method and apparatus for creating a representative heartbeat obtains ECG data from a plurality of ECG waveforms, which are in turn obtained from signals received from a plurality of ECG electrodes. QRS detection logic detects heartbeats in the ECG data. Classification logic classifies heartbeats into categories based on shape and/or timing. Alignment logic aligns the heartbeats. This logic slides the heartbeats occurring at various times across a stationary alignment template to calculate when the heartbeats are best aligned, and performs adjustments to reduce the effects of noise or jitter on the different ECG waveforms. Representative heartbeat creation logic creates a representative heartbeat from the aligned heartbeats. This logic time slices through the aligned heartbeats, discarding a percentage of the smallest and largest magnitudes of the aligned heartbeats at each instance of time, and averaging the remaining magnitudes to produce a representative heartbeat. This trimmed averaging technique results in a high quality representative beat, since samples from noise and misclassified beats are discarded. The representative heartbeat is displayed, either alone or with head rate and/or other measurement information, to the cardiologist or medical professional for diagnosis of the condition of the patient's head, such as a diagnosis of coronary artery disease, based on finding a depressed ST segment in the representative heartbeat of a patient undergoing a stress or exercise test.

31 Claims, 24 Drawing Sheets

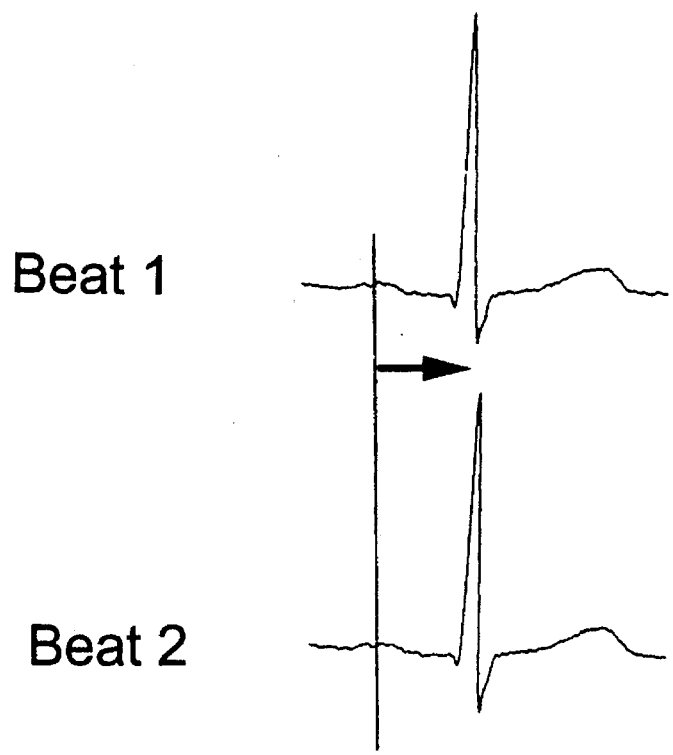
Beat 1
Beat 2
Fig. 17
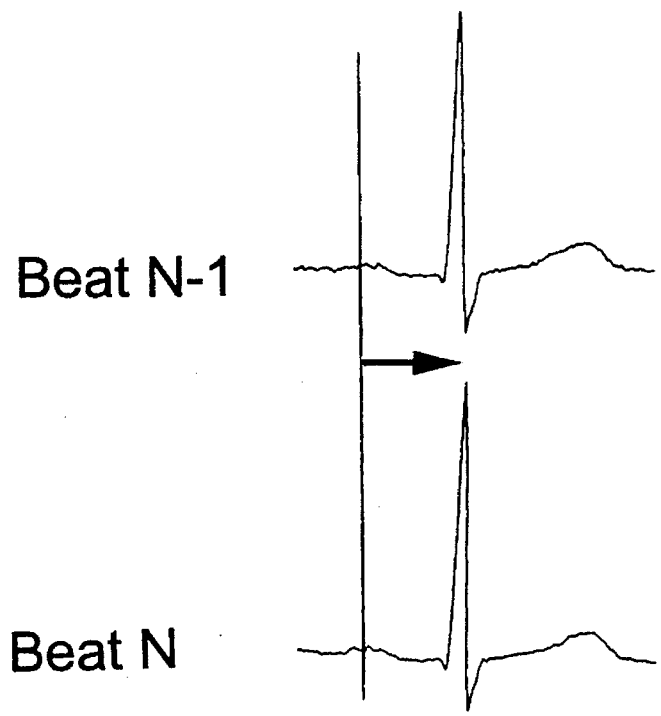
Beat N-1
Beat N

ST LEVEL: −2.5mm
ST SLOPE: 45mm/sec
ST INTERGRAL: 0.3cm2
HEART RATE: 112bpm

METHOD AND APPARATUS FOR CREATING A REPRESENTATIVE HEARTBEAT FROM AN ECG WAVEFORM

CROSS REFERENCE TO RELATED APPLICATIONS

This application is related to the following commonly assigned patent applications, filed on even date herewith:

| Title | Ser. No. |
| --- | --- |
| Method And Apparatus For Detecting Heartbeats In An ECG Waveform | 564,889 |
| Method And Apparatus For Calculating A Heart Rate In An ECG Waveform | 564,749 |
| Method And Apparatus For Classifying Heartbeats In An ECG Waveform | 564,768 |
| Method And Apparatus For Obtaining Heartbeat Measurements From An ECG Waveform | 564,774 |

FIELD OF THE INVENTION

This invention relates to the electronics circuitry field. More particularly, this invention is a method and apparatus for creating a representative heartbeat from an ECG waveform.

BACKGROUND OF THE INVENTION

Designers of medical instrumentation such as cardiographs face many difficult challenges in their jobs. The devices they design are expected to deliver high quality information about the electrical activity of a patient's heart to a cardiologist or other medical professional, so that a correct diagnosis of the condition of the patient's heart can be made. Unfortunately, the ECG electrodes connected to a patient usually deliver ECG data to a cardiograph that comprise not only information showing the electrical activity of the patient's heart, but also electrical noise. This noise can make up most of the ECG data, and can corrupt and totally overwhelm the portion of the ECG data that contain information about the electrical activity of a patient's heart. This problem is especially acute in hostile environments, such as a patient undergoing a stress or exercise test, where the noise can be quite extreme. Unless the medical instrumentation designers are successful at designing a medical instrument that analyzes this ECG data to eliminate or reduce the effects of this noise, the cardiologist or other medical professional will find it difficult, if not impossible, to obtain information about a patient's heart, such as a representative heartbeat, that is usable in arriving at a correct diagnosis of the condition of the patient's heart.

SUMMARY OF THE INVENTION

A method and apparatus for creating a representative heartbeat obtains ECG data from a plurality of ECG waveforms, which are in turn obtained from signals received from a plurality of ECG electrodes. QRS detection logic detects heartbeats in the ECG data. Classification logic classifies heartbeats into categories based on shape and/or timing. Alignment logic aligns the heartbeats. This logic slides the heartbeats occurring at various times across a stationary alignment template to calculate when the heartbeats are best aligned, and performs adjustments to reduce the effects of noise or jitter on the different ECG waveforms. Representative heartbeat creation logic creates a representative heartbeat from the aligned heartbeats. This logic time slices through the aligned heartbeats, discarding a percentage of the smallest and largest magnitudes of the aligned heartbeats at each instance of time, and averaging the remaining magnitudes to produce a representative heartbeat. This trimmed averaging technique results in a high quality representative beat, since samples from noise and misclassified beats are discarded. The representative heartbeat is displayed, either alone or with heart rate and/or other measurement information, to the cardiologist or medical professional for diagnosis of the condition of the patient's heart, such as a diagnosis of coronary artery disease, based on finding a depressed ST segment in the representative heartbeat of a patient undergoing a stress or exercise test.

DESCRIPTION OF THE DRAWINGS

FIG. 17 shows a graph of exemplary aligned heartbeats being timesliced by the representative heartbeat creation logic of the preferred embodiment of the invention.

DETAILED DESCRIPTION OF THE PREFERRED EMBODIMENT

I. Overview

Figure 1:
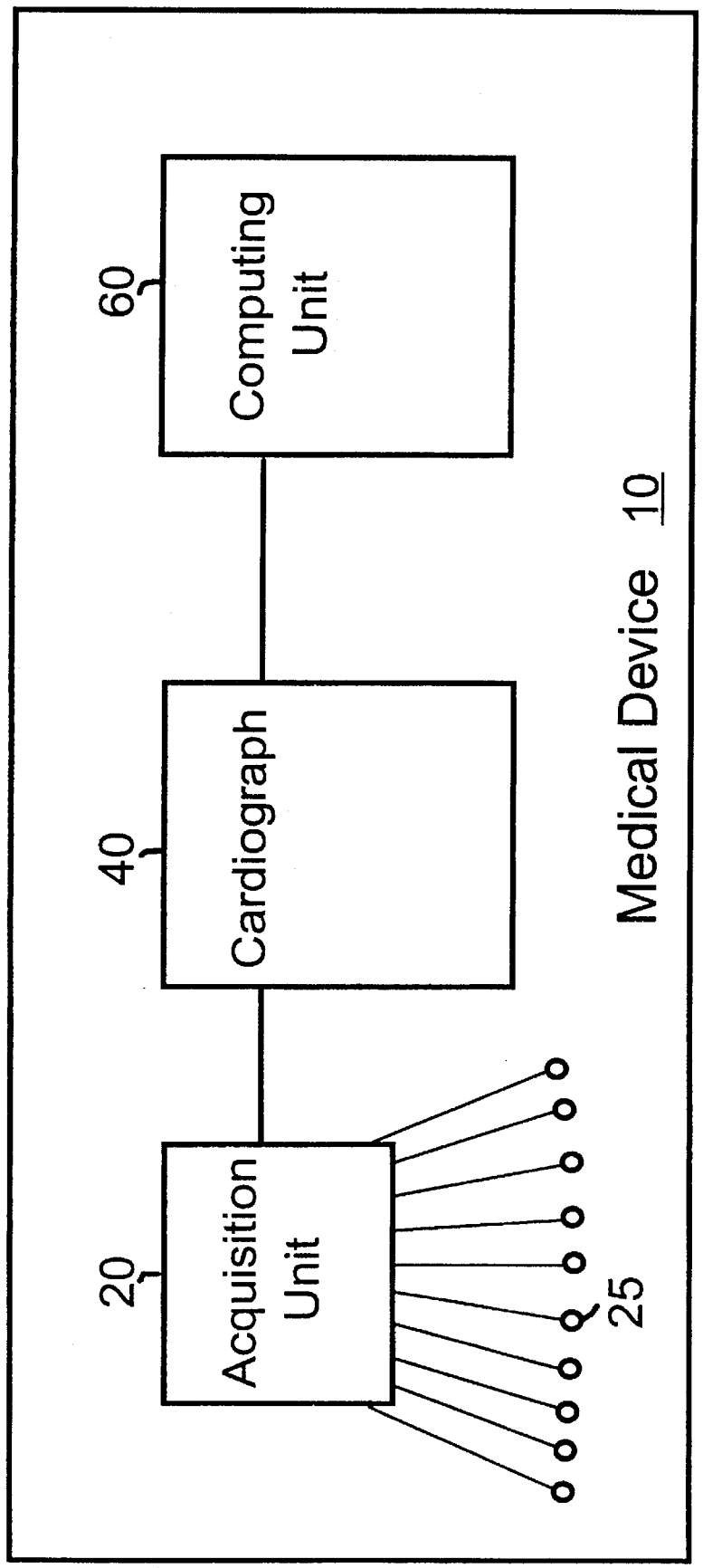
FIG. 1 shows a block diagram of the medical device of the preferred embodiment of the invention.

FIG. 1 shows a block diagram of the medical device of the preferred embodiment of the invention. Medical device 10 comprises acquisition unit 20, electrodes 25, cardiograph 40, and computing unit 60. In the preferred embodiment, cardiograph 40 and acquisition unit 20 are separate components of a PageWriter XLi, manufactured by the Hewlett-Packard company, modified to execute the flowcharts of FIGS. 4 and 12 of the preferred embodiment of the invention. Computing unit 60 is a HP Vectra personal computer, suitably programmed to execute the flowcharts of FIGS. 5–11 of the preferred embodiment of the invention.

Figure 2:
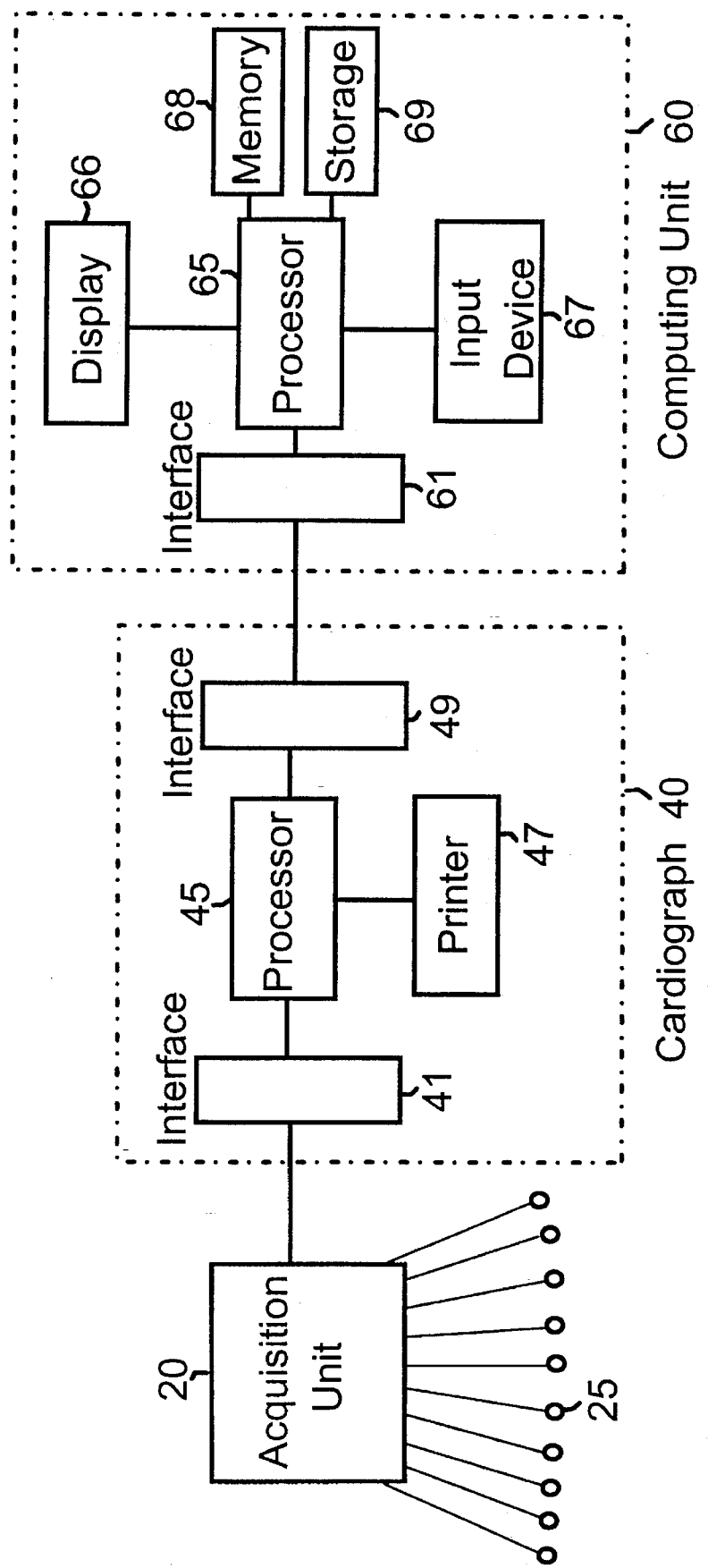
FIG. 2 shows a block diagram of the medical device of FIG. 1 in more detail.

FIG. 2 shows a block diagram of medical device 10 in more detail. Cardiograph 40 contains acquisition unit interface 41, processor 45, printer 47, and computing unit interface 49. Processor 45 executes the flowcharts of FIGS. 4 and 12 of the preferred embodiment of the invention. Computing unit 60 contains cardiograph interface 61, processor 65, display 66, input device 67, memory 68, and storage 69. Processor 65 executes the flowcharts of FIGS. 5–11 of the preferred embodiment of the invention. While FIG. 2 shows medical device 10 as containing discrete components, those skilled in the art will appreciate that medical device 10 could be a single unit that contains each of the components shown in FIG. 2, or contain a different number of discrete components, and still fall within the spirit and scope of the invention.

Figure 3:
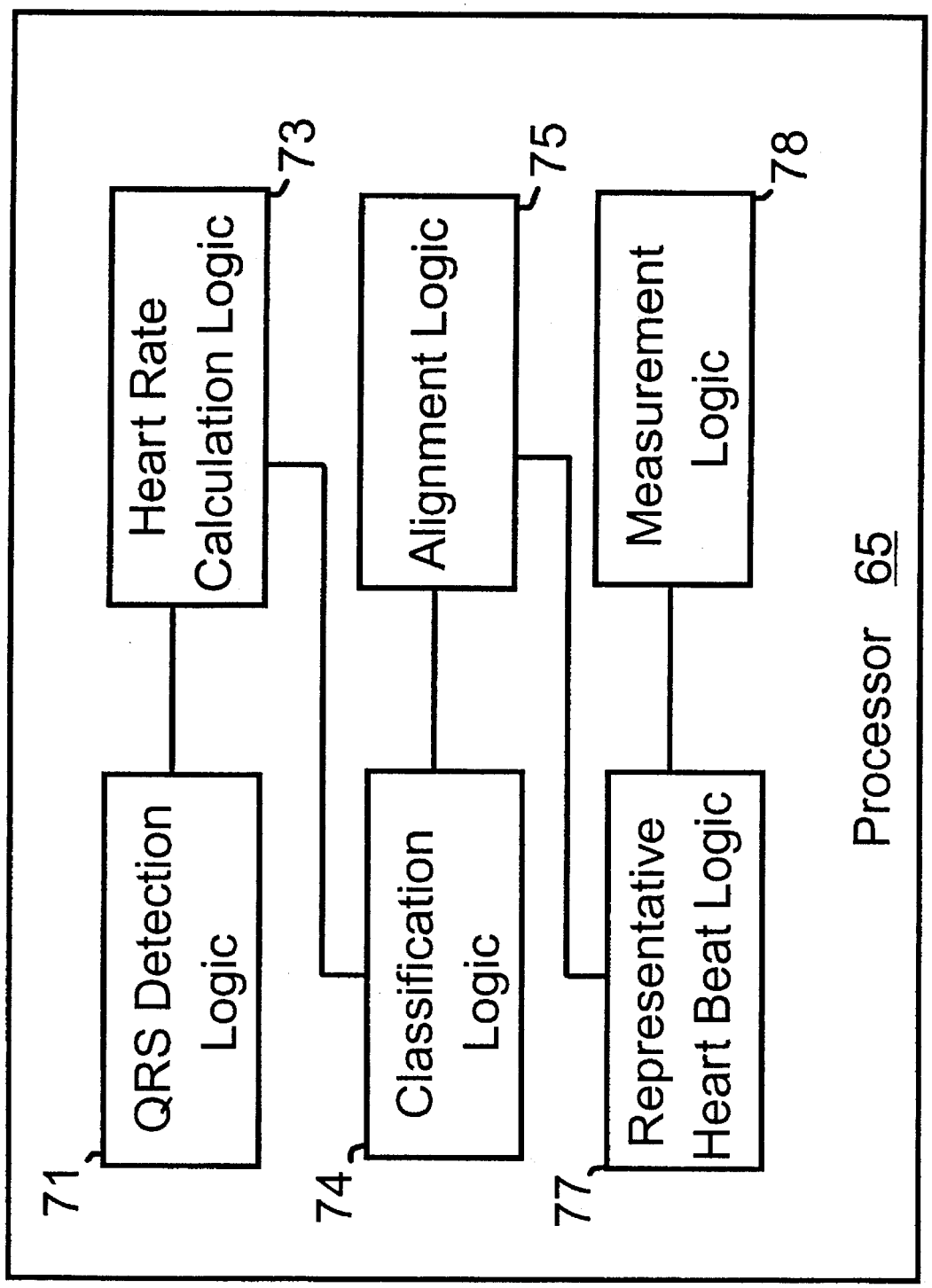
FIG. 3 shows the processor of the computing unit of the medical device of FIG. 2 in more detail.

FIG. 3 shows processor 65 of computing unit 60 of medical device 10 in more detail. Processor 65 contains QRS detection logic 71, heart rate calculation logic 73, classification logic 74, alignment logic 75, representative heartbeat creation logic 77, and measurement logic 78. In the preferred embodiment, each of these logic blocks is performed by software written to perform the functions of relevant portions of the flowcharts shown in FIGS. 5–11, and this software is executed by processor 65. Alternatively, some or all of logic blocks 71–78 could be special purpose hardware, such as contained in an application specific integrated circuit, designed to perform functions of relevant portions of the flowcharts shown in FIGS. 5–11.

Figure 4:
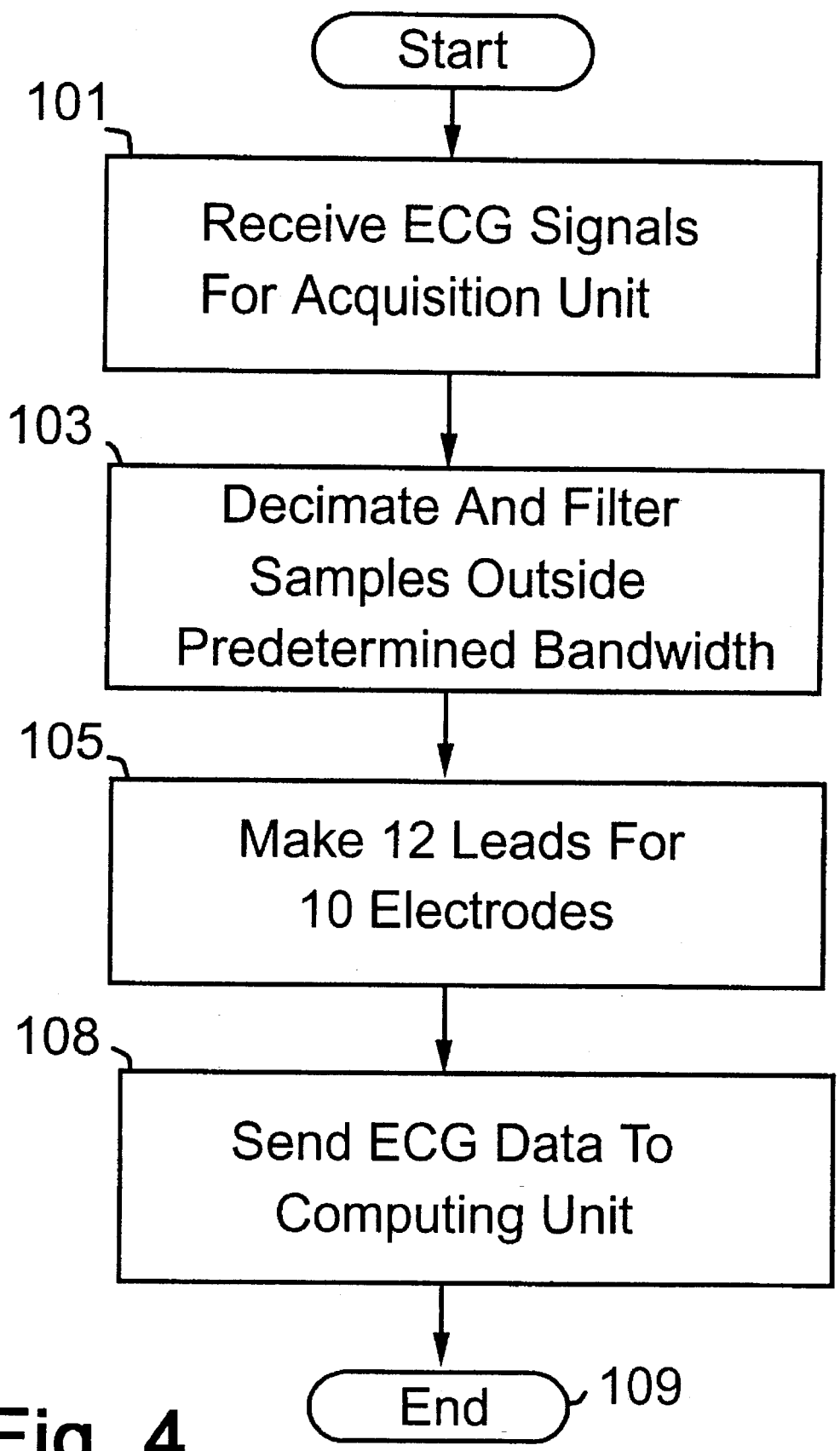
FIGS. 4 and 12 show flowcharts of the operation of the cardiograph of the preferred embodiment of the invention.

FIG. 4 shows a flowchart of the operation of cardiograph 40 of the preferred embodiment of the invention. In block 101, ECG signals are received from electrodes 25 of acquisition unit 20. In the preferred embodiment, these signals are digital signals sampled at a high sampling rate. Block 103 decimates and filters the sampled ECG signals outside of a predetermined bandwidth. In the preferred embodiment, the predetermined bandwidth is 0.01 Hz to 150 Hz, and the decimation process reduces the number of samples to one eighth of the number of original samples. Block 105 makes twelve ECG leads from the ten electrodes in a conventional manner. The signals contained on the twelve ECG leads will be referred to herein as "ECG waveforms", and the information contained thereon will be referred to herein as "ECG data". Those skilled in the art will appreciate that the actual number of electrodes or leads may be different than discussed above and still fall within the spirit and scope of the invention. Block 108 sends the ECG data on the ECG waveforms to computing unit 60. The flowchart ends in block 109.

Figure 5:
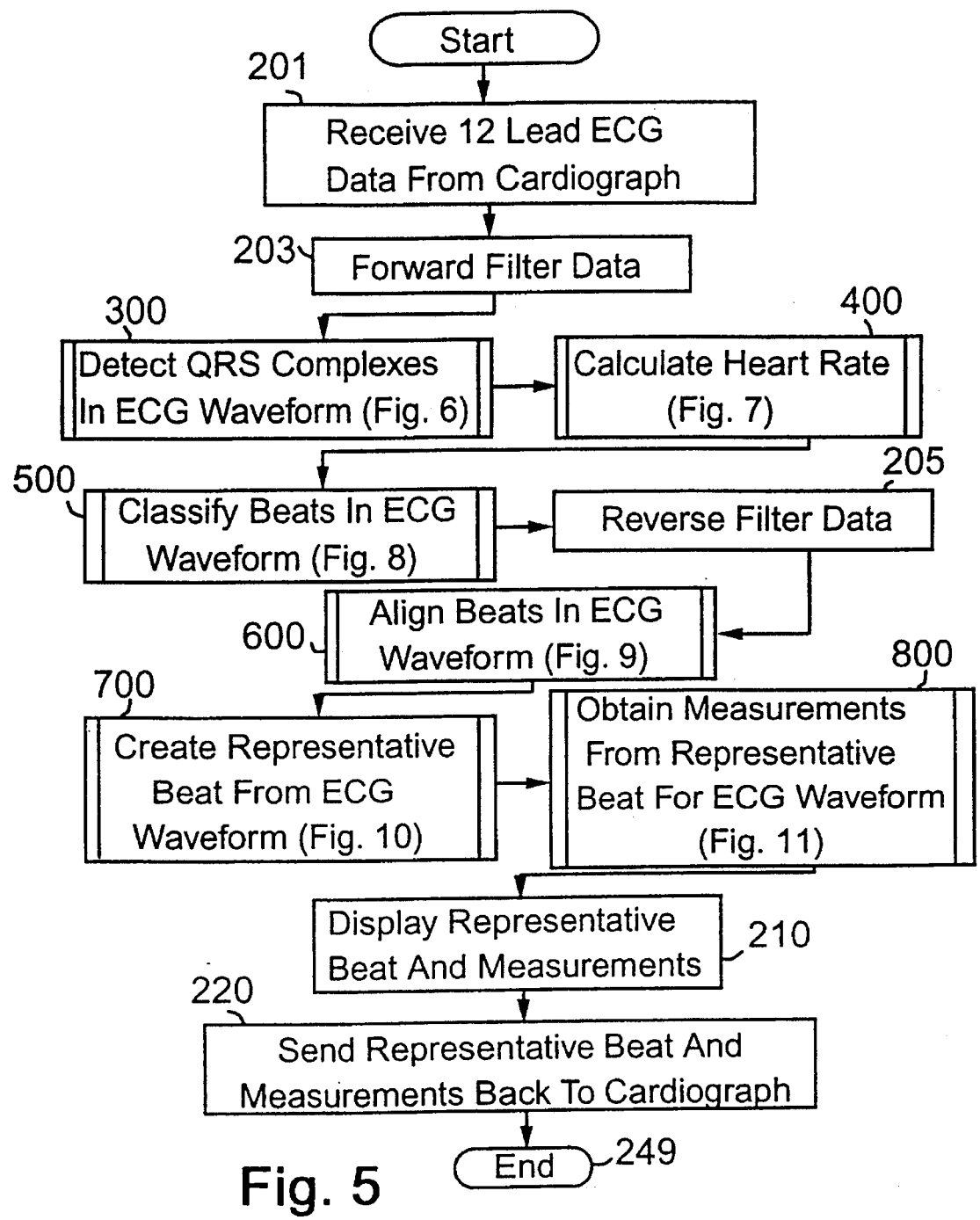
FIG. 5 shows a high level flowchart of the operation of the computing unit of the preferred embodiment of the invention.

FIG. 5 shows a high level flowchart of the operation of computing unit 60 of the preferred embodiment of the invention. Block 201 receives the ECG waveforms containing the ECG data from cardiograph 40. Block 203 forward filters the ECG data. In the preferred embodiment, this filter is a high pass filter used as part of a forward/reverse filtering scheme to remove baseline wander while preserving low frequency information in the ECG data. Block 300 calls a subroutine that detects the heartbeats (i.e. QRS complexes) in the ECG waveforms. This subroutine calculates an activity function from a subset of the ECG waveforms determined to be least noisy, and uses this activity function to search for heartbeats. This allows for true heartbeats to be detected while discarding false "noise" beats. The operation of this subroutine will be described in more detail later in conjunction with the discussion of FIGS. 6A–6B.

Block 400 calls a subroutine that calculates the patient's heart rate. This logic determines the intervals between the heartbeats, discards a percentage of the shortest and longest intervals, and averages the remaining intervals to arrive at the patient's heart rate. This results in a robust calculation of the heart rate even in the presence of noise falsely detected as heartbeats and missed beats common in noisy environments. The operation of this subroutine will be described in more detail later in conjunction with the discussion of FIGS. 7A–7B.

Block 500 calls a subroutine that classifies heartbeats. This classification is done by comparing each heartbeat against a group of templates corresponding to one or more heartbeat classifications. The templates are updated to track changes in the morphology of the heartbeats. The operation of this subroutine will be described in more detail later in conjunction with the discussion of FIGS. 8A–8C.

Block 205 reverse filters the ECG data. In the preferred embodiment, this filter is a high pass filter used as part of a forward/reverse filtering scheme to remove baseline wander while preserving low frequency information in the ECG data.

Block 600 calls a subroutine that aligns heartbeats prior to representative heartbeat creation. This logic slides the heartbeats across an alignment template heartbeat to calculate when the heartbeats are aligned, and performs adjustments to reduce the effects of noise or jitter on the different ECG waveforms. The operation of this subroutine will be described in more detail later in conjunction with the discussion of FIGS. 9A–9B.

Block 700 calls a subroutine that creates a representative heartbeat from the aligned heartbeats. This logic time slices through the aligned heartbeats, discarding a percentage of the smallest and largest magnitudes of the aligned heartbeats at each instance of time and averaging the remaining magnitudes to produce a representative heartbeat. This trimmed averaging technique results in a high quality representative beat, since samples from noise and misclassified beats are discarded. The operation of this subroutine will be described in more detail later in conjunction with the discussion of FIGS. 10A–10B.

Block 800 calls a subroutine that measures various aspects of a representative heartbeat. This logic analyzes the representative heartbeats from a group of ECG waveforms to determine an earliest QRS onset and latest QRS offset, and uses these values to perform a variety of measurements. This results in robust measurements even in very noisy environments. The operation of this subroutine will be described in more detail later in conjunction with the discussion of FIGS. 11A–11B.

Block 210 displays the representative heartbeat created by subroutine 700 and, optionally, the measurements obtained by subroutines 800 and 400, on display 66 of computing unit 60 (FIG. 2). Examples of these displays are shown in FIGS.

18 and 19. Block 220 sends the representative heartbeat and measurements for each ECG waveform, including the heart rate measurement calculated by subroutine 400, back to cardiograph 40. Cardiograph 40 processes this information in accordance with the flowchart of FIG. 12. The flowchart ends in block 249.

Figure 12:
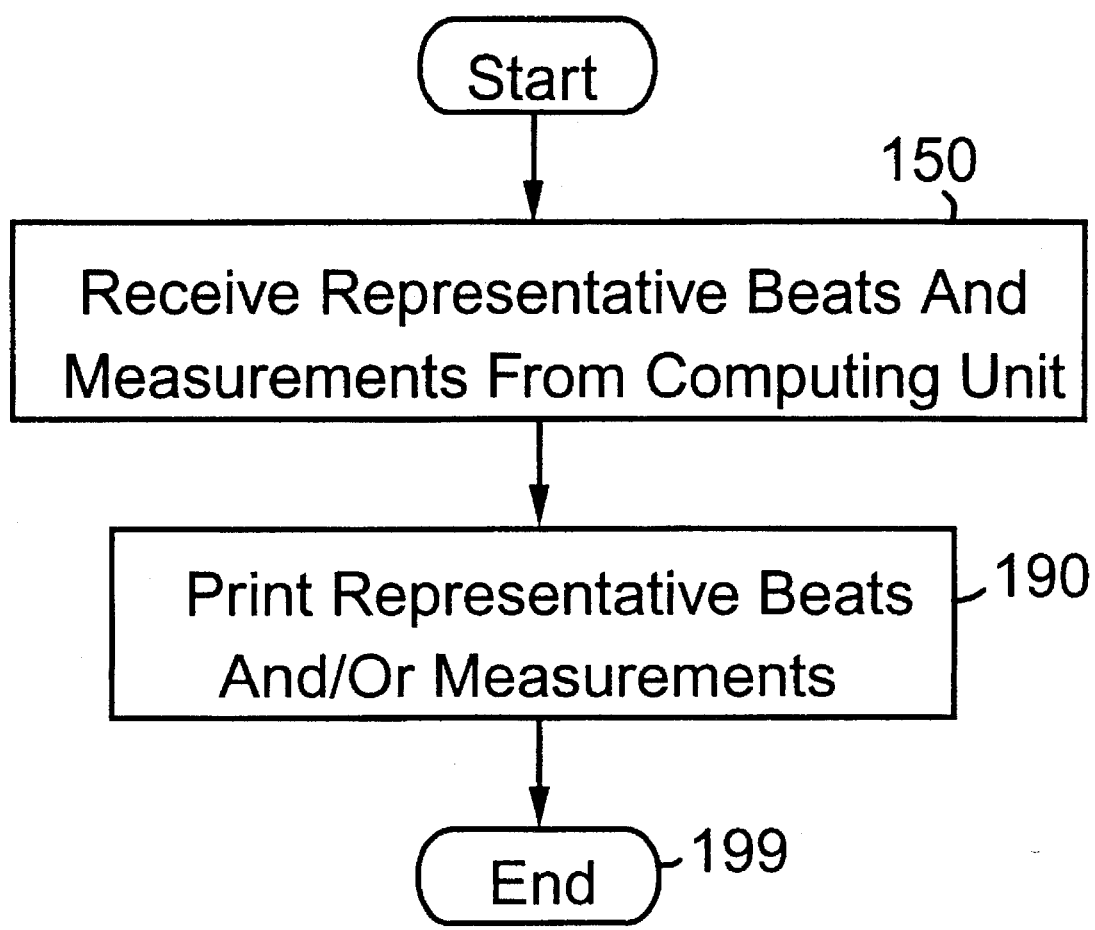
Figure 18:
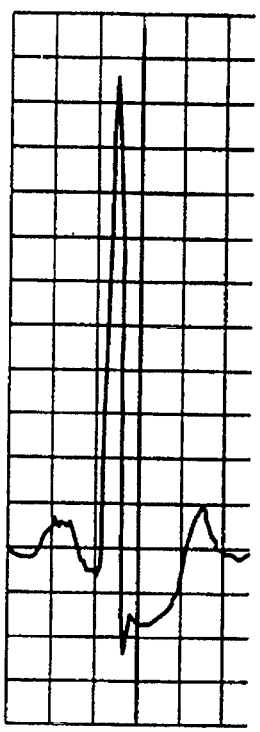
FIG. 18 shows a printout or display of a representative heartbeat without measurements.
Figure 19:
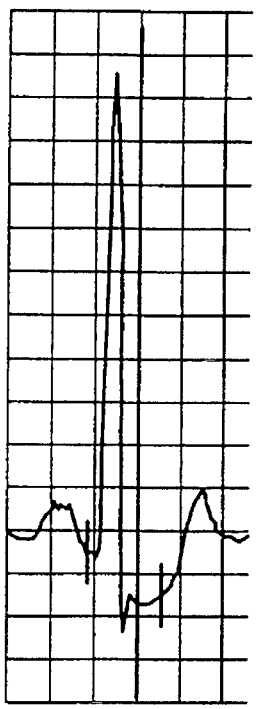
FIG. 19 shows a printout or display of a representative heartbeat with measurements.

FIG. 12 shows how cardiograph 40 processes the information received from computing unit 60. Block 150 receives the representative heartbeat and measurements, including the heart rate measurement, sent by block 220 of FIG. 5. Block 190 prints the representative heartbeat created by subroutine 700 and, optionally, the measurements obtained by subroutines 800 and 400, on printer 47 of cardiograph 40 (FIG. 2). Examples of these printouts are shown in FIGS. 18 and 19.

II. QRS Detection

Figure 6A:
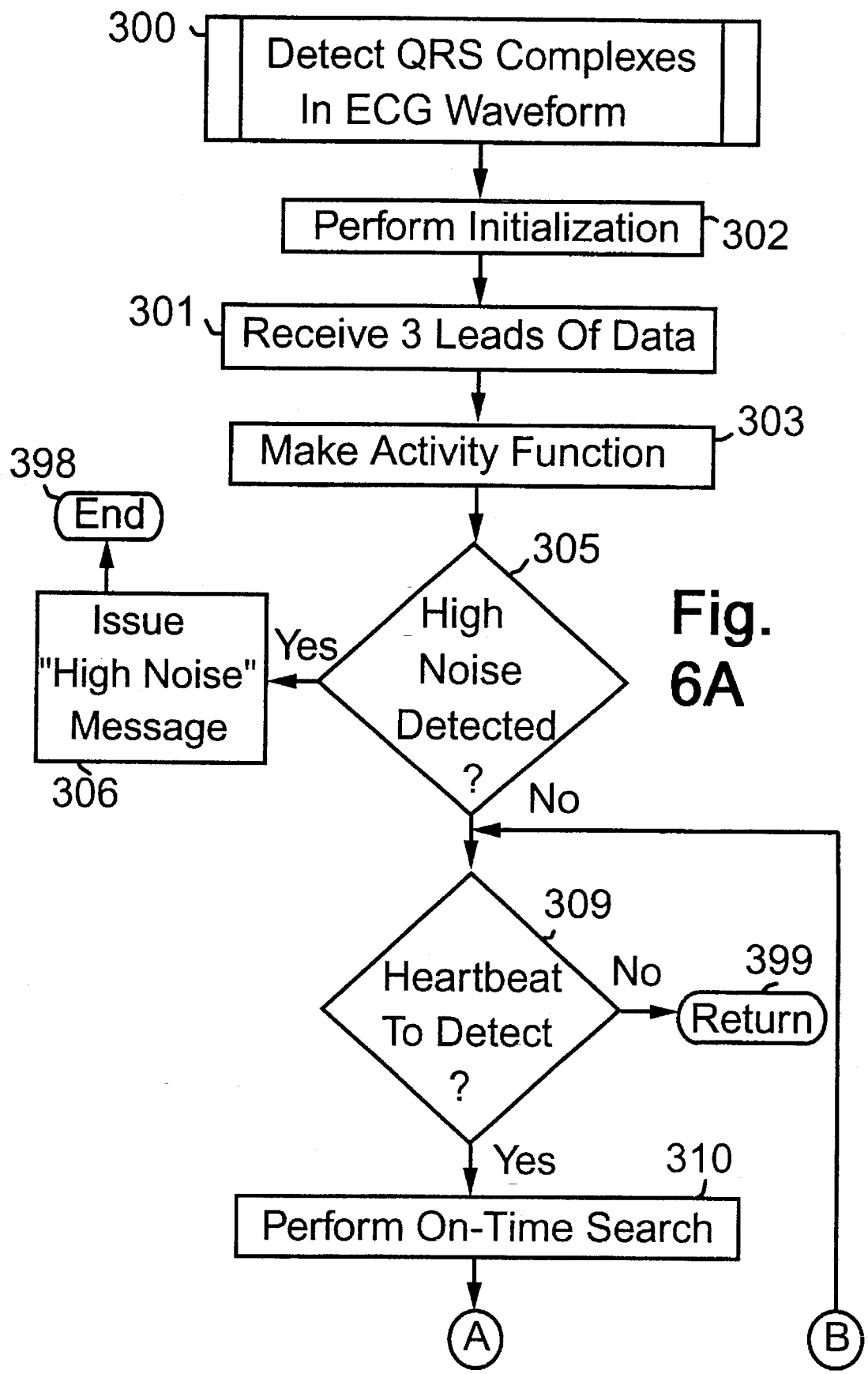
FIGS. 6A and 6B show a flowchart of the operation of the QRS detection logic of the preferred embodiment of the invention.
Figure 6B:
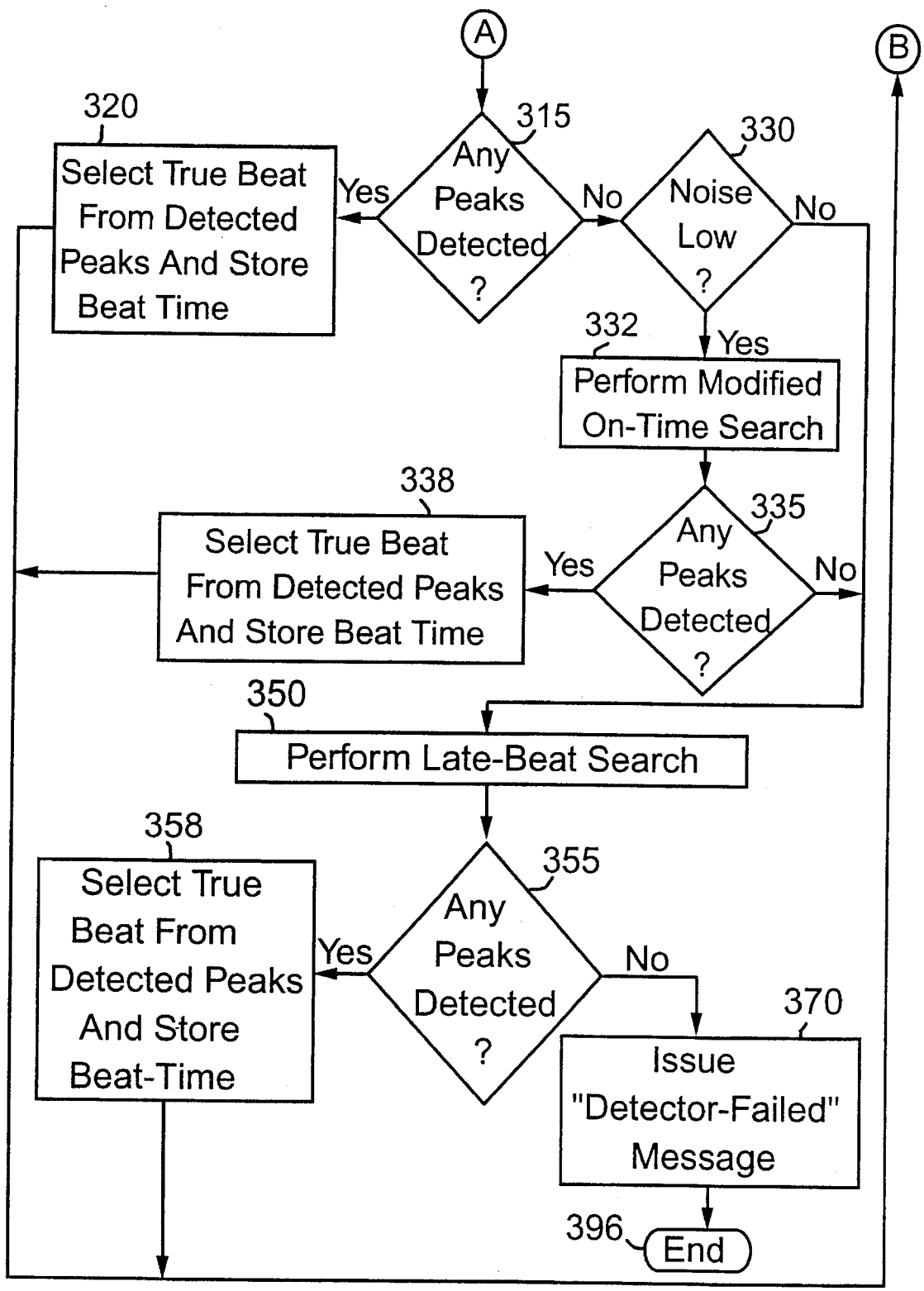
Figure 13:
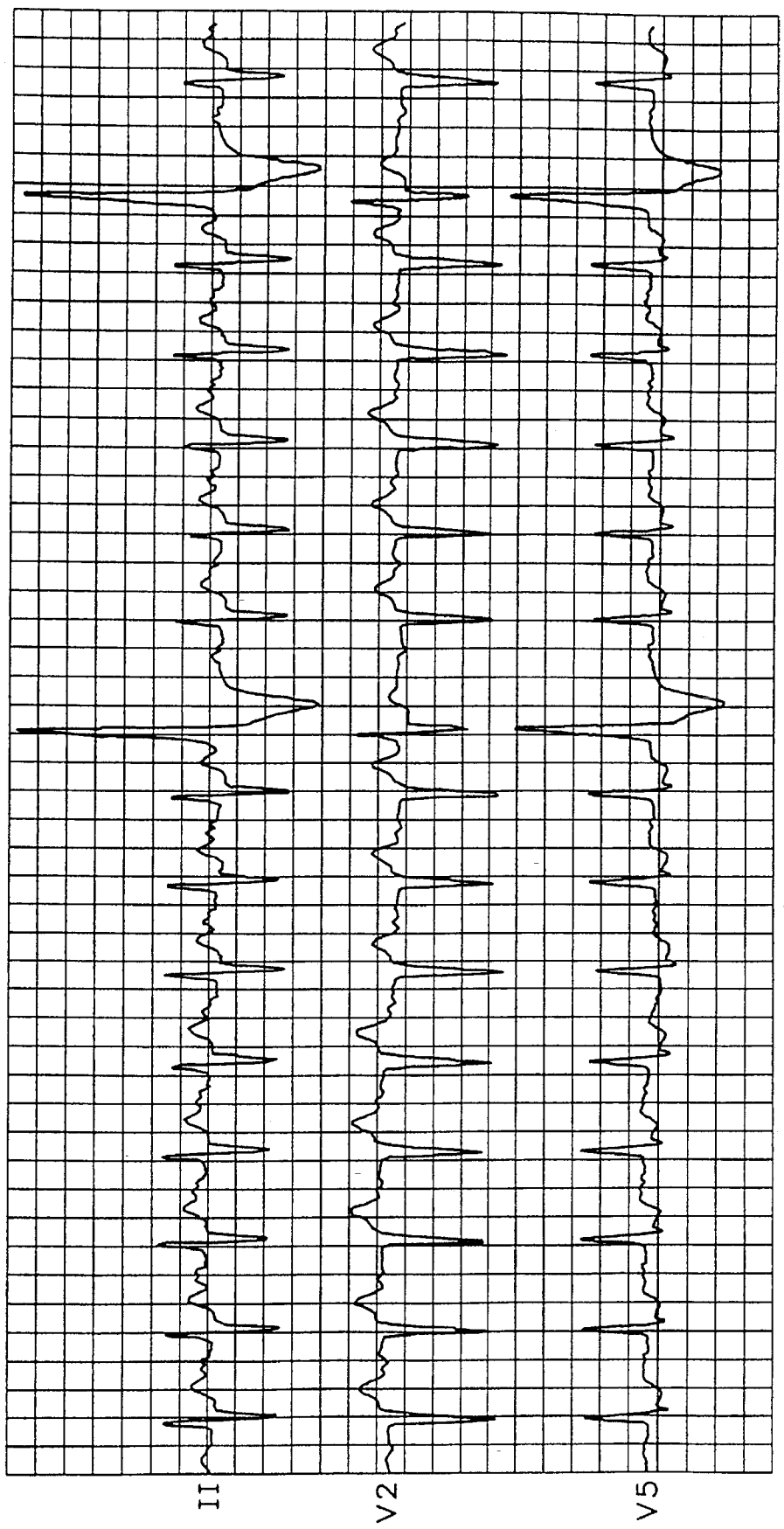
FIG. 13 shows a graph of three exemplary ECG waveforms used by the QRS detection logic of the preferred embodiment of the invention.

FIGS. 6A–6B shows a flowchart of the operation of subroutine 300, performed by QRS detection logic 71 of computing unit 60 of the preferred embodiment of the invention. Block 302 performs an initialization process that learns about the ECG data. More specifically, the first time through the subroutine, this process analyzes the first few seconds of ECG data to determine a preliminary interval between peaks and the magnitude of an average peak. During routine processing (i.e. subsequent times through the subroutine) block 302 continues to update the information obtained the first time through the subroutine. Block 301 receives ECG data from three ECG waveforms out of the twelve ECG waveforms received by computing unit 60 in block 201 (FIG. 4). A graph of three exemplary ECG waveforms is shown in FIG. 13. In the preferred embodiment, block 301 selects these three ECG waveforms as the three ECG waveforms that have optimal noise characteristics. This is done by continuously calculating the signal quality on the twelve ECG waveforms and ranking these waveforms from highest to lowest signal quality.

Figure 14:
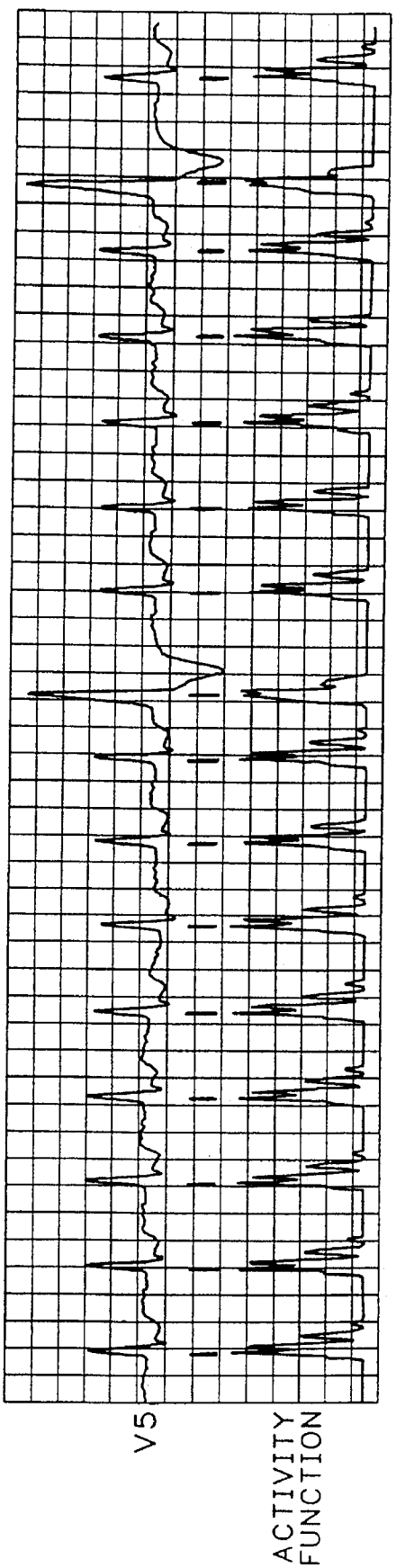
FIG. 14 shows a graph of an exemplary activity function used by the QRS detection logic of the preferred embodiment of the invention.

Block 303 calculates an activity function out of the three leads of ECG data. An activity function is a signal mathematically derived from the ECG data which emphasizes characteristics of the heartbeat while minimizing the influence of noise to enable more accurate heartbeat detection. In the preferred embodiment, the activity function is created by decimating the ECG data by one half, filtering the data using a bandpass filter and taking the absolute value of the first difference. The absolute first differences from the three ECG waveforms are then summed together, thresholded and smoothed to improved noise performance. Noise statistics (i.e., signal quality) across all twelve ECG waveforms are calculated and updated. A graph of an exemplary activity function is shown in FIG. 14.

Block 305 checks the noise statistics to see if unacceptably high noise was detected. If so, block 306 issues a "high noise" message, which is displayed on display 66 of computing unit 60 (FIG. 2). This error causes the subroutine to terminate abnormally by ending in block 398. In the absence of high noise, block 305 is answered negatively. Block 309 looks to see if it is to detect another heartbeat. If not, the subroutine returns in block 399 to block 400 of FIG. 5.

If block 309 is answered affirmatively, subroutine 300 performs up to three different types of searches to find each heartbeat. The first search is an on-time search. This search is normally used to detect heartbeats that appear within a small window of their expected time. If the on-time search fails to detect a heartbeat, a modified on-time search is used. The modified on-time search is similar in operation to the on-time search, but can detect heartbeats in low noise environments that the on-time search might miss, such as early beats. If both the on-time search and the modified on-time search fail to detect a heartbeat, a late beat search is performed. This search detects heartbeats that appear later than their expected time.

The operation of the on-time search will now be discussed in more detail. Block 310 performs an on-time search of the activity function for QRS complexes in the ECG data. In the preferred embodiment, block 310 searches over 115% of the current interval length between heartbeats (as determined in block 302) with a threshold that starts at 80% of the average peak value of the activity function. The threshold is then linearly decreased over time to 40% at the end of the search window. Any local maxima discovered above this linearly decreasing threshold is considered a "peak".

Block 315 checks to see if any peaks were detected. If so, block 320 selects the true heartbeat (i.e., QRS peak) from the detected peaks by looking at the times each peak occurred. Those skilled in the art will appreciate that the above-described search could detect multiple peaks in a noisy environment, all but one of which would be noise. The peak that occurred closest to the time the next heartbeat was expected is considered a true heartbeat, and timing information about this heartbeat is stored in storage 69 of computing unit 60 (FIG. 2). Flow of control loops back to block 309 to look for another beat to detect.

Referring again to FIGS. 6A–6B, the operation of the modified on-time search will now be discussed. If block 315 is answered negatively, block 330 checks to see if the noise level is low. If so, block 335 searches the activity function by using a modified on-time search. In the preferred embodiment, this search is performed by using a constant lower threshold, such as 54% of the average peak activity function value, over 115% of the current interval length. Block 335 checks to see if any peaks were detected. If so, block 338 selects the true heartbeat from the detected peaks by selecting the peak that occurred closest to the time the next heartbeat was expected. Information about the heartbeat selected in block 338, such as beat timing information, is stored in storage 69 of computing unit 60 (FIG. 2). Flow of control loops back to block 309 to look for another beat to detect.

The operation of the late beat search will now be discussed. If either blocks 330 or 335 are answered negatively, block 350 performs a late beat search. In the preferred embodiment, this block searches the activity function over three R—R interval lengths using a linearly decreasing threshold, as was done with the on-time search. Block 355 checks to see if any peaks were detected. If so, block 358 selects the true heartbeat from the detected peaks by selecting the first peak that it finds. Information about the heartbeat selected in block 358, such as beat timing information, is stored in storage 69 of computing unit 60 (FIG. 2). Flow of control loops back to block 309 to look for another beat to detect. If block 355 is answered negatively, block 370 issues a "detector failed" message that is displayed on display 66 of computing unit 60. Since no beats were detected, this causes an abnormal termination of the subroutine in block 396.

III. Heart Rate Calculation

Figure 7A:
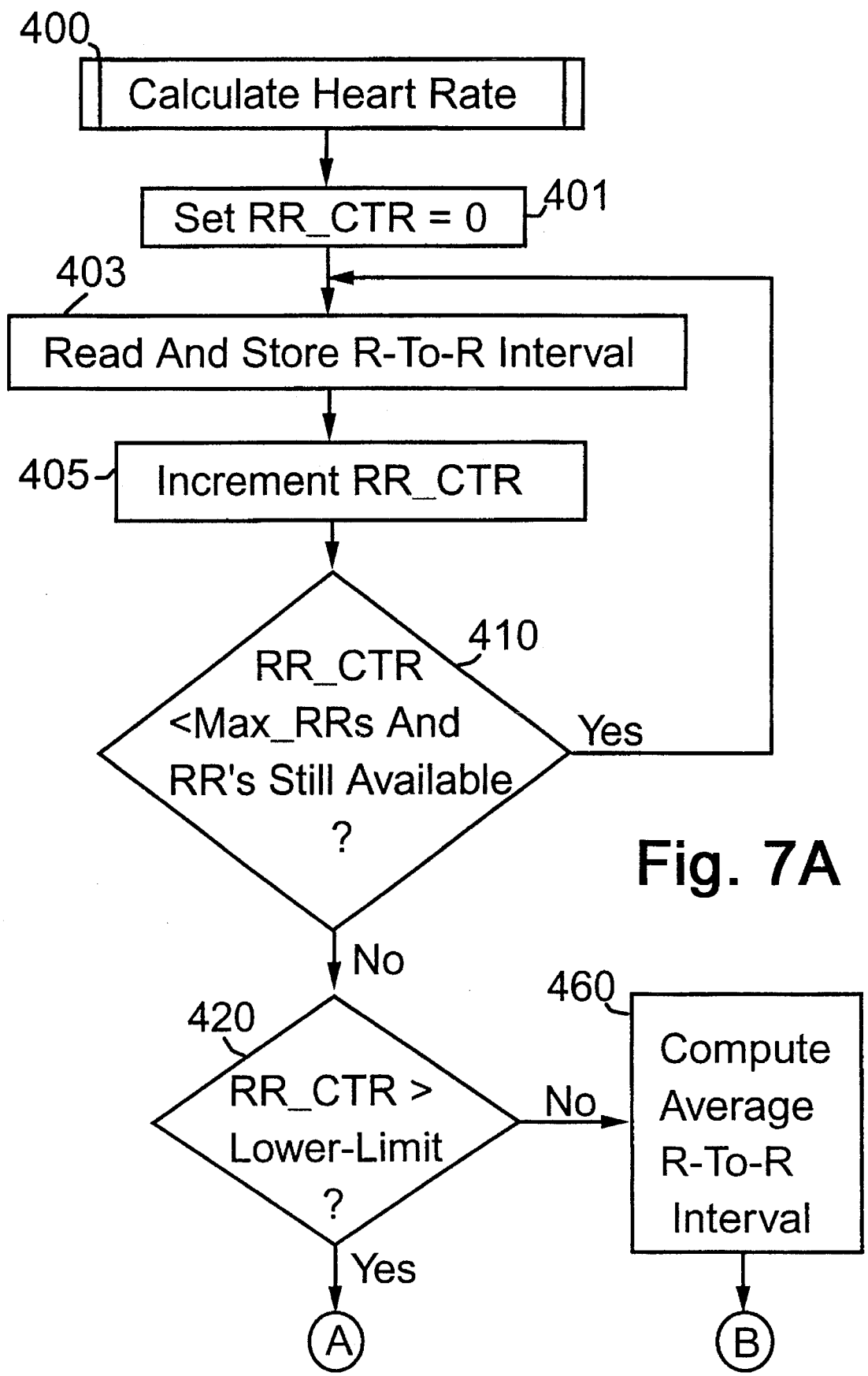
FIGS. 7A and 7B show a flowchart of the operation of the head rate calculation logic of the preferred embodiment of the invention.
Figure 7B:
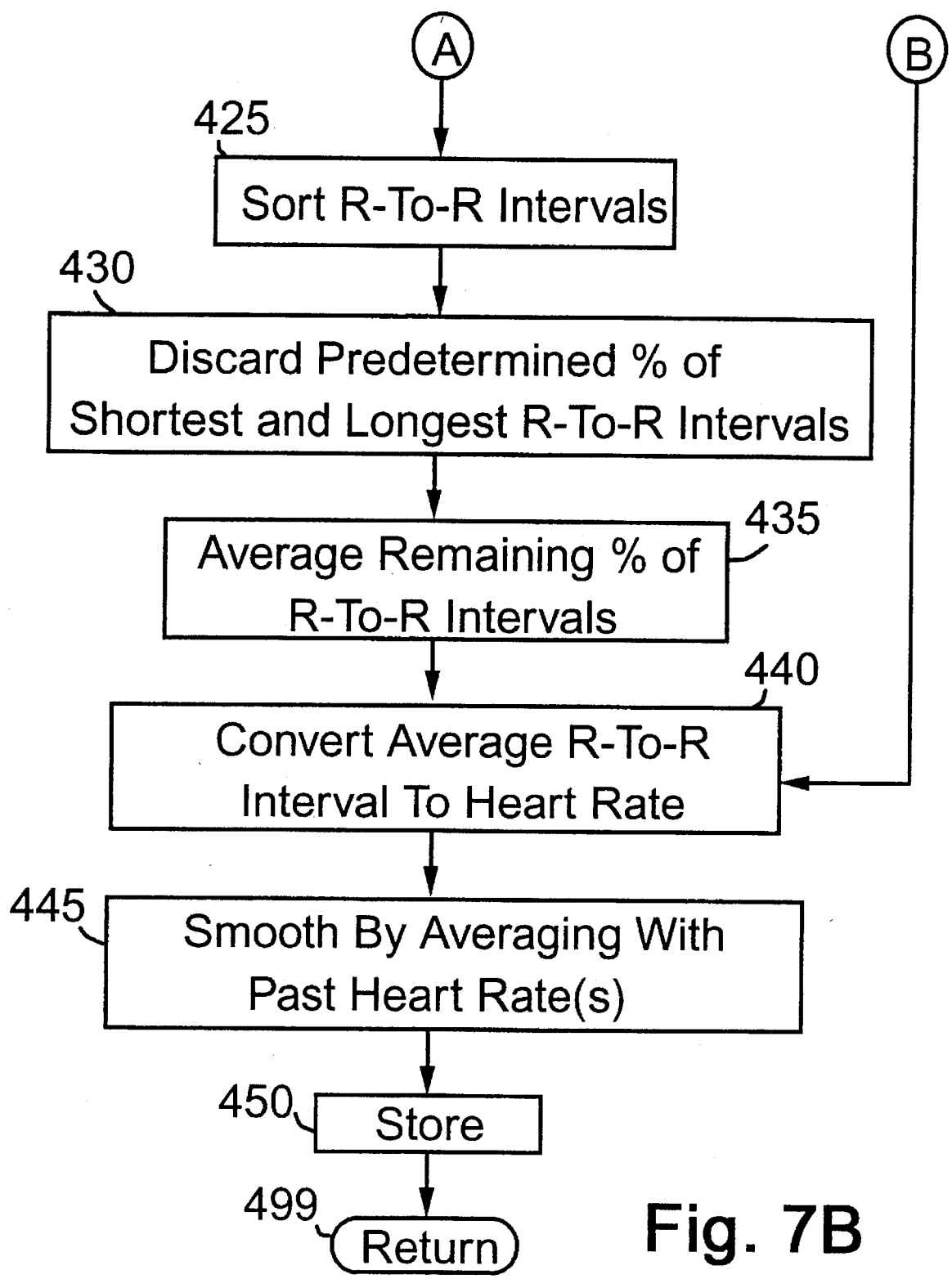

FIGS. 7A–7B show a flowchart of the operation of subroutine 400, performed by the heart rate calculation logic 73 of computing unit 60 of the preferred embodiment of the invention. Block 401 sets a counter called RR_ctr=0. Block 403 reads and stores the R—R interval between the first heartbeat detected in the ECG waveform and the second heartbeat detected in the ECG waveform. In the preferred embodiment, this detection is done using information stored by QRS detection logic 71 in subroutine 300, although conventional methods of detecting R—R intervals in an ECG waveform could also be used. Block 405 increments RR_ctr. Block 410 checks to see if the counter is less than a maximum counter value and there are additional heartbeats still available for analysis in the ECG waveform. If both of these conditions are true, flow of control loops back to block 403 until one condition is no longer true. An alternate embodiment has been contemplated where block 403 is a timer and where block 410 checks to see if a maximum time has elapsed. For example, if a maximum time was set for 10 seconds, only heartbeats occurring in the most recent 10 second period of time are used to calculate the heart rate.

When block 410 is eventually answered negatively, block 420 checks to make sure at least a minimum number of heartbeats were analyzed by the loop made up of blocks 403–410.

If block 420 is answered affirmatively, block 425 sorts the R—R intervals from shortest to longest. Block 430 then discards a percentage of the shortest and longest R—R intervals. In a noisy environment, the QRS detector may incorrectly detect noise as a heartbeat, and may incorrectly miss a real heartbeat. These errors result in incorrect R—R intervals, both too short and too long. The trimmed average done here results in a robust and accurate heart rate calculation even in the presence of false detections and missed beats. With low noise and/or arrhythmias, this trimmed average technique also produces an accurate calculation of the heart rate.

In the preferred embodiment, block 430 discards 25% of the shortest and 25% of the longest R—R intervals, although different values could be used. Block 435 then averages the remaining R—R intervals. Block 440 converts this average R—R interval to a heart rate. Block 445 smoothes the heart rate determined by block 440 by averaging it with a predetermined number of past heart rates. In the preferred embodiment, block 445 averages the current heart rate with the past two heart rates. In any event, the heart rate determined by block 445 (or by block 440, if the smoothing step of block 445 is not desired) is stored by block 450 in storage 69 of computing unit 60 (FIG. 2). The subroutine returns in block 499 to block 500 of FIG. 5.

If block 420 is answered negatively, block 460 simply computes the average interval of the small number of R—R intervals that were read and stored in block 403. This average R—R interval is converted to a heart rate in block 440, and the heart rate is stored by block 450 in storage 69 of computing unit 60 (FIG. 2). As before, the subroutine returns in block 499 to block 500 of FIG. 5.

IV. Heartbeat Classification

Figure 8A:
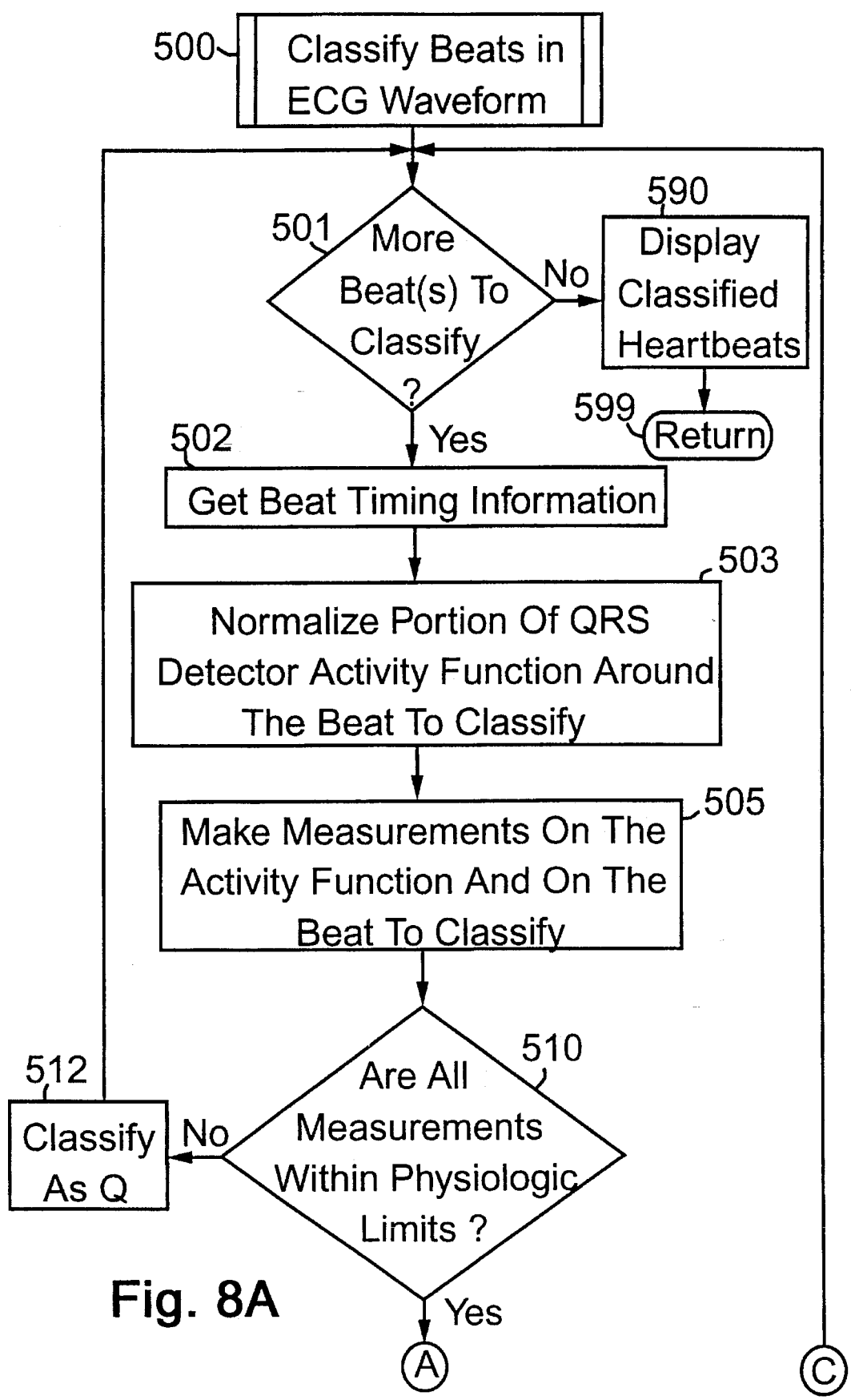
FIGS. 8A–8C show a flowchart of the operation of the classification logic of the preferred embodiment of the invention.
Figure 8B:
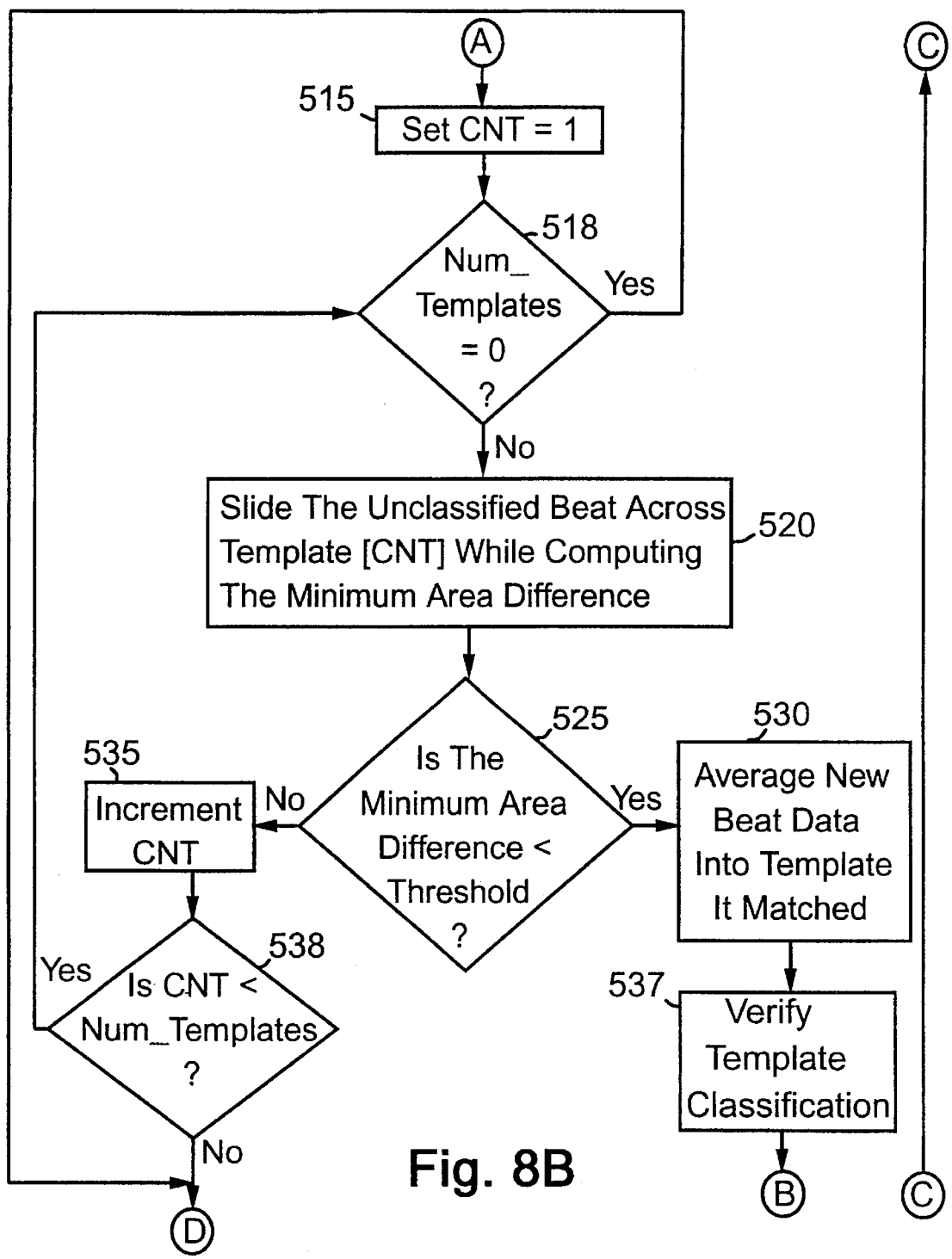
Figure 8C:
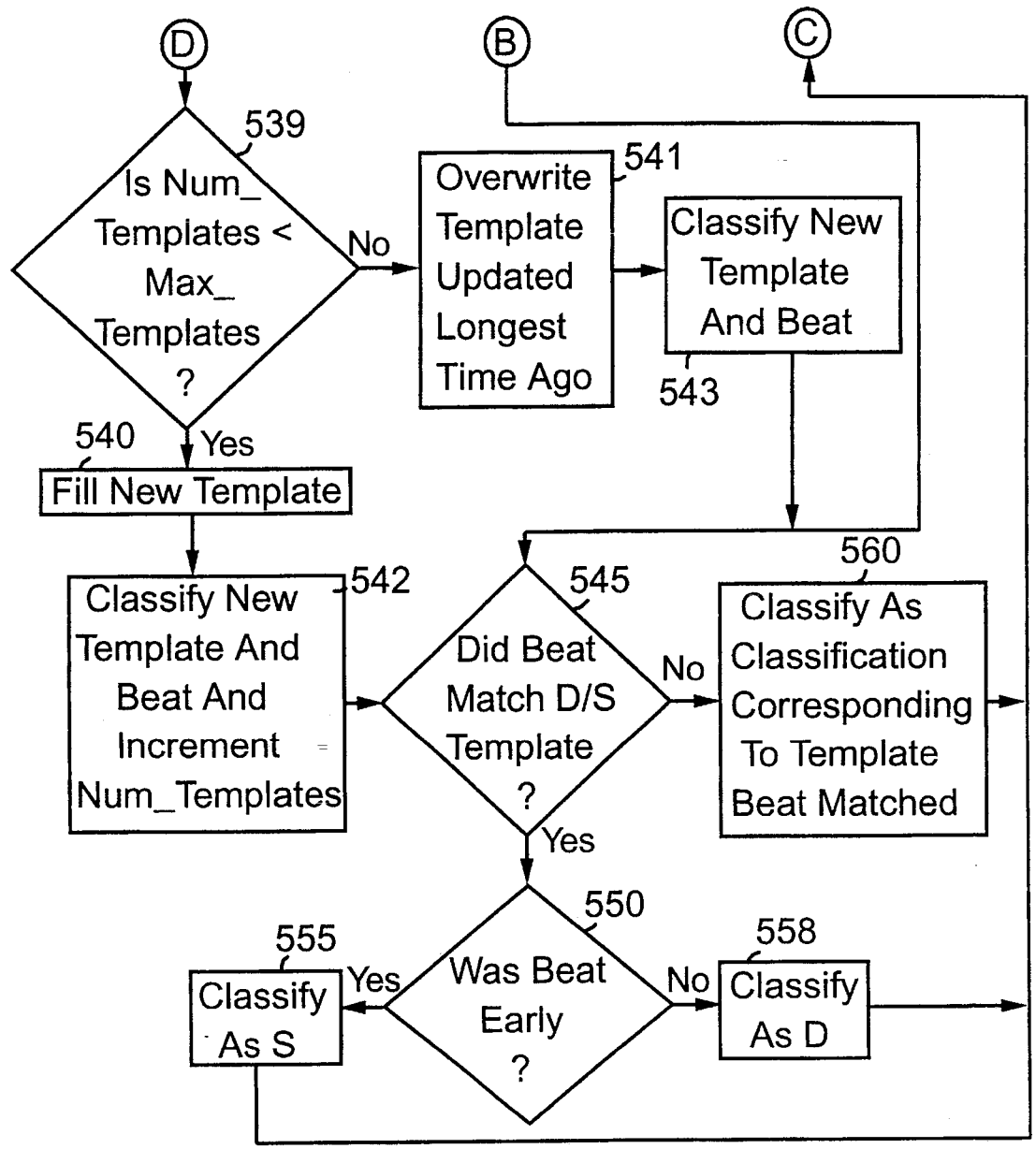

FIGS. 8A–8C shows a flowchart of the operation subroutine 500, performed by classification logic 74 of computing unit 60 of the preferred embodiment of the invention. In the preferred embodiment, subroutine 500 is used to classify beats as "D" (dominant), "V" (ventricular ectopic), "S" (supraventricular ectopic), or "Q" (questionable), although other classifications could be used.

Block 501 checks to see if there are more heartbeats to classify. If so, Block 502 gets beat timing information for the next heartbeat. In the preferred embodiment, this information is obtained from QRS detection logic 71 in a manner that has already been discussed, although conventional methods of obtaining this information could also be used. Block 503 normalizes the portion of the activity function (from QRS detection logic 71 or conventional means) around the beat to classify. Block 505 performs timing and physiologic measurements on both the activity function and on the beat to classify. These measurements are used in blocks 510 and 550 to assist in beat classification, as will be discussed later.

Block 510 checks to see if all measurements made by block 505 are within physiologic limits (e.g. within a predetermined width and height). If not, the beat is classified as questionable ("Q"), due to noise, and flow of control loops back to block 501 to see if there are more beats to classify. If block 510 is answered affirmatively, block 515 sets a template counter to 1, initializing a series of steps that compares the beat to classify with one or more templates. Block 518 checks to see if a counter called Num_templates=0. If so, no templates have yet been created for this ECG waveform, and flow of control skips down to blocks 539 and 540 to create a new template by saving this beat as the first template. Block 542 then uses timing and physiologic information to classify this beat and template as either "D" (Dominant), "V" (ventricular ectopic), "S" (supraventricular ectopic), or "Q" (questionable). Most commonly, this beat will be classified as D and the template classified as D/S, for "Dominant/supraventricular ectopic", since the vast majority of beats classified will be classified this way, and since both D and S beats have the same morphology and thus would match the same template, but vary by timing information—the S beat being earlier than the D beat. The method of distinguishing between D and S beats is performed by blocks 545 to 558, as will be discussed in more detail later. Those skilled in the art will appreciate that more than one template can be classified as "D/S", since dominant heartbeats can have more than one unique morphology. Block 542 increments Num_Template to one to indicate one stored template. Flow of control moves to block 545, the operation of which will be discussed later.

Once at least one template is created, block 518 is answered negatively, and block 520 slides the beat to classify across the first, stationary template. As previously discussed, the first template usually corresponds to a first heartbeat classification of D/S, meaning the template for dominant and supraventricular waveforms. As block 520 slides this beat across the first template, the minimum area difference between the beat to classify and the first template is calculated. Block 525 asks if this minimum area difference is less than a threshold. If it is, the beat matches the first (D/S) template, and block 530 averages the new beat data into the template it matched. In the preferred embodiment, a weighted average is used, where the existing template is given more weight in the averaging process than the new beat. Block 530 also keeps track of the number of times a beat matched this template, as well as when a beat most recently matched this template.

If block 525 is answered negatively, block 535 increments the template counter. Block 538 verifies that the maximum number of templates to check has not been exceeded, which would indicate all templates have been checked. If block 538 is answered affirmatively, flow of control loops back to blocks 518 and 520, where the beat is slid across the second template. The second template exemplarily corresponds to a classification of ventricular ectopic ("V"). Block 520 again computes the minimum area difference, and block 525 again asks if this minimum area difference is less than a threshold. If it is, the beat matches the second (V) template, and block 530 averages the new beat data into the template it matched. If no match was found, the subroutine loops through blocks 535, 538, 518, 520, and 525 until a match is found or until block 538 is answered negatively, indicating that all existing templates have been checked for matches.

Once a match is found and block 530 averages the new beat data into the template it matched, block 537 verifies the classification of the template. As new beats are averaged into the existing templates, it is possible for the classification of the template to change. For example, a template originally classified as "V" may be reclassified to "D" as more beats are averaged into it. Block 545 checks to see if the beat matched a D/S template. If so, an additional inquiry about the beat must be made before the beat can be classified. This is done in block 550, which asks if the beat was early. If so, the beat is classified as supraventricular ("S") in block 555, and flow of control loops back to block 501 to look to see if there are more beats to classify. If not, the beat is classified as dominant ("D") in block 558, and flow of control loops back to block 501 to look to see if there are more beats to classify. If block 545 determined that the beat matched a template other than the D/S template, block 560 classifies the beat as the classification corresponding to the template it matched. For example, if the beat matched the ventricular ectopic ("V") template, the beat would be classified as ventricular ectopic. Flow of control loops back to block 501, as previously discussed.

Referring again to block 538, if block 538 is answered negatively, all existing templates have been checked and none of them match. Block 539 then asks if Num_template is less than Max_template—a counter indicating the maximum number of templates. If not, block 540 creates a new template for this beat. Block 542 classifies the new template and beat and increments Num_templates, as discussed previously.

If block 539 is answered negatively, the maximum number of templates has been reached. Block 541 overwrites the template with the least recent update. Like block 542, block 543 classifies the new template, but does not increment Num_templates, since the number of templates did not change. Those skilled in the art will appreciate that the number of templates actually created can vary, depending on the amount of noise in the environment and whether any ectopic beats are detected.

Figure 15:
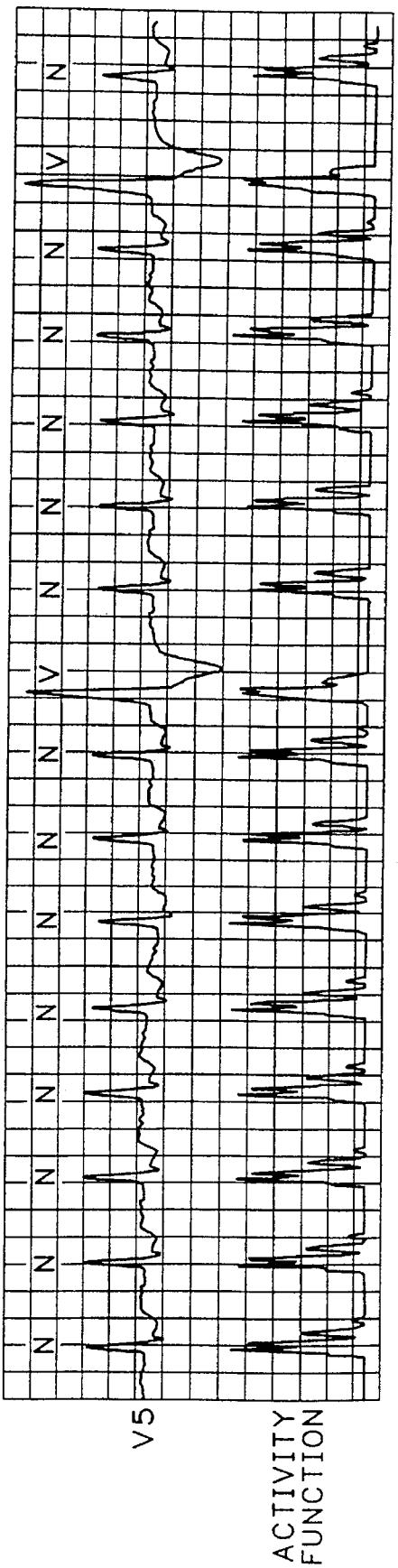
FIG. 15 shows a graph of exemplary classified heartbeats.

When block 501 determines that there are no more beats to classify, block 590 displays the classified heartbeats on display 66 of computing unit 60 (FIG. 2). One such exemplary display is shown in FIG. 15. The subroutine returns in block 599 to block 205 of FIG. 5.

V. Beat Alignment

Figure 9A:
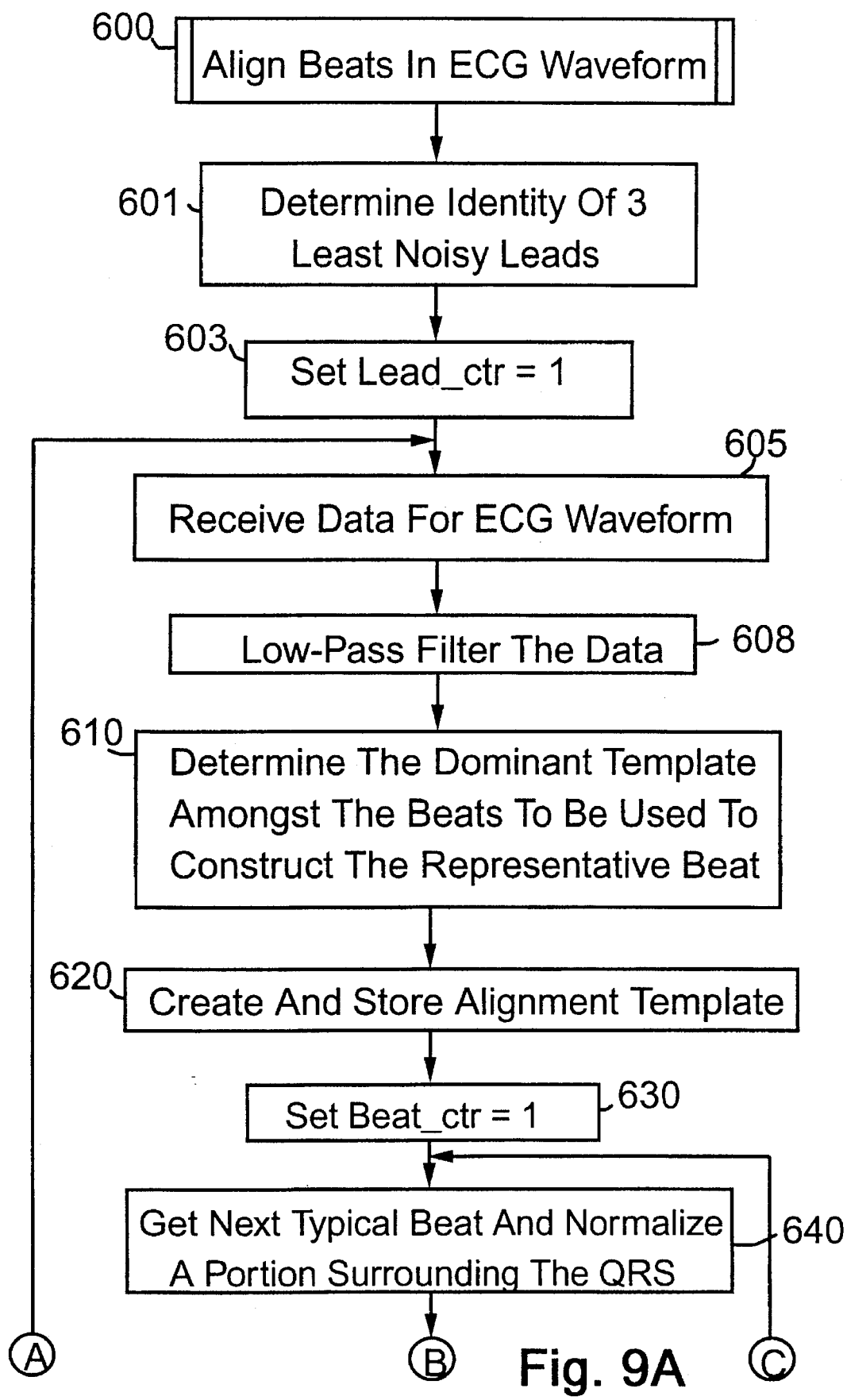
FIGS. 9A–9B show a flowchart of the operation of the alignment logic of the preferred embodiment of the invention.
Figure 9B:
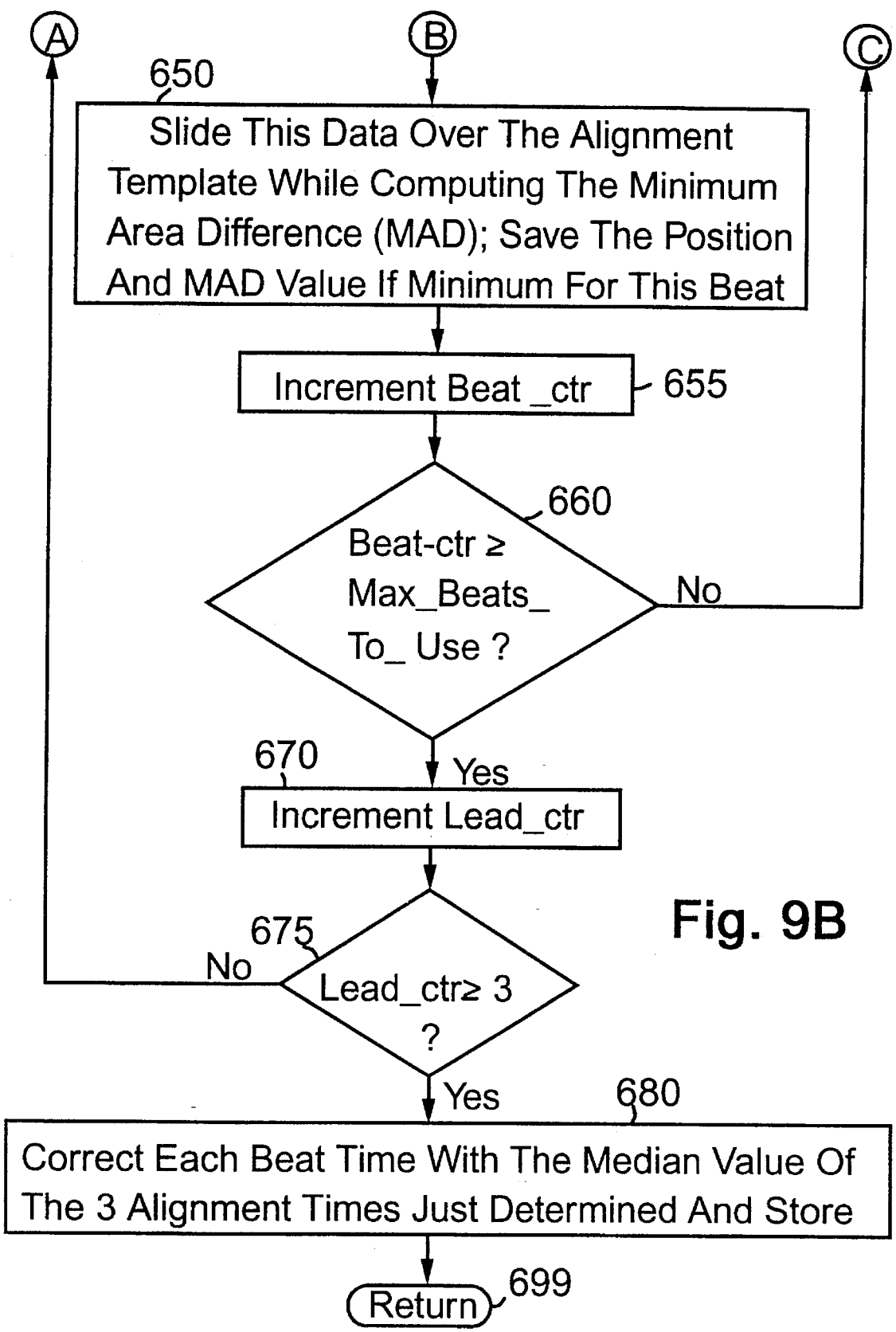

FIGS. 9A–9B show a flowchart of the operation of subroutine 600, performed by alignment logic 75 of computing unit 60 of the preferred embodiment of the invention. Block 601 determines which 3 ECG waveforms are the least noisy. the preferred embodiment, this is done by using the information obtained in block 301 of the Detect QRS Complexes in EGG Waveform subroutine 300, although this determination could be made directly in this subroutine by continuously calculating the signal to noise ratio or other indication of signal quality on the twelve EGG waveforms and ranking these waveforms from highest to lowest, or by using some other technique. Block 603 sets a lead counter to look at the first of the three least noisy ECG waveforms. Block 605 receives ECG data from the ECG waveform determined by the lead counter. After the ECG data is low pass filtered in block 608, block 610 determines the dominant template amongst the beats to be used to construct the representative heartbeat. In the preferred embodiment, this is done by looking at the number of times the templates used by the classification logic were matched by a beat, as determined in block 530 in FIG. 8B. By definition, this will be a D/S template.

Block 620 creates and stores an alignment template in storage 69 of computing unit 60. In the preferred embodiment, the alignment template is created with a beat which matched the dominant template determined in block 610, where a portion of the dominant template around the QRS is normalized. An alternate embodiment has been contemplated where step 610 is skipped, and block 620 creates an alignment template by finding the first beat classified as D (via beat classification logic 74 or a conventional method of beat classification) and using this beat as the alignment template.

Block 630 sets a beat counter to 1. Block 640 gets the next dominant beat for this ECG waveform and normalizes a portion of this beat around the QRS complex. For the purposes of this application, beats classified as "D" are referred to herein as "dominant", while beats classified as "V", "S", or "Q" are referred to as "non-dominant". In the preferred embodiment, non-dominant beats are excluded from alignment and from the determination of a representative heartbeat, since these beats can contaminate the representative heartbeat.

Block 650 slides this beat across the stationary alignment template, while computing the value of the sum of the absolute values of the difference between the beat and the alignment template. This value is referred to herein as the area difference. The position where the area difference is the minimum (Minimum Area Difference) is the position where the beat is best aligned with the alignment template, and this position is saved for this beat in storage 69 of computing unit 60. Block 655 increments the beat counter. Block 660 checks to see if the beat counter is greater than or equal to the number of beats to align for this ECG waveform. If not, flow of control loops back to block 640 to get the next dominant beat. If so, block 670 increments the lead counter.

Figure 16:
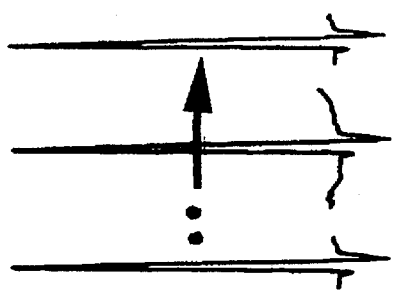
FIG. 16 shows a graph of exemplary heartbeats being aligned by the alignment logic of the preferred embodiment of the invention.

Block 675 checks to see if the lead counter is greater than or equal to 3—the number of least noisy ECG waveforms selected in block 601. If block 675 is answered negatively, flow of control loops back to block 605, where the alignment process is repeated for the next ECG waveform. If block 675 is answered affirmatively, block 680 corrects and stores each beat time on each ECG waveform with the median value of the alignment times just determined independently on the three least noisy leads. This is done to minimize the effect of noise which results in beats on different ECG waveforms best aligning at slightly different times (i.e. jitter). The subroutine returns in block 699 to block 700 in FIG. 5. FIG. 16 shows a new beat being slid across a stationary template.

VI. Representative Beat Creation

Figure 10A:
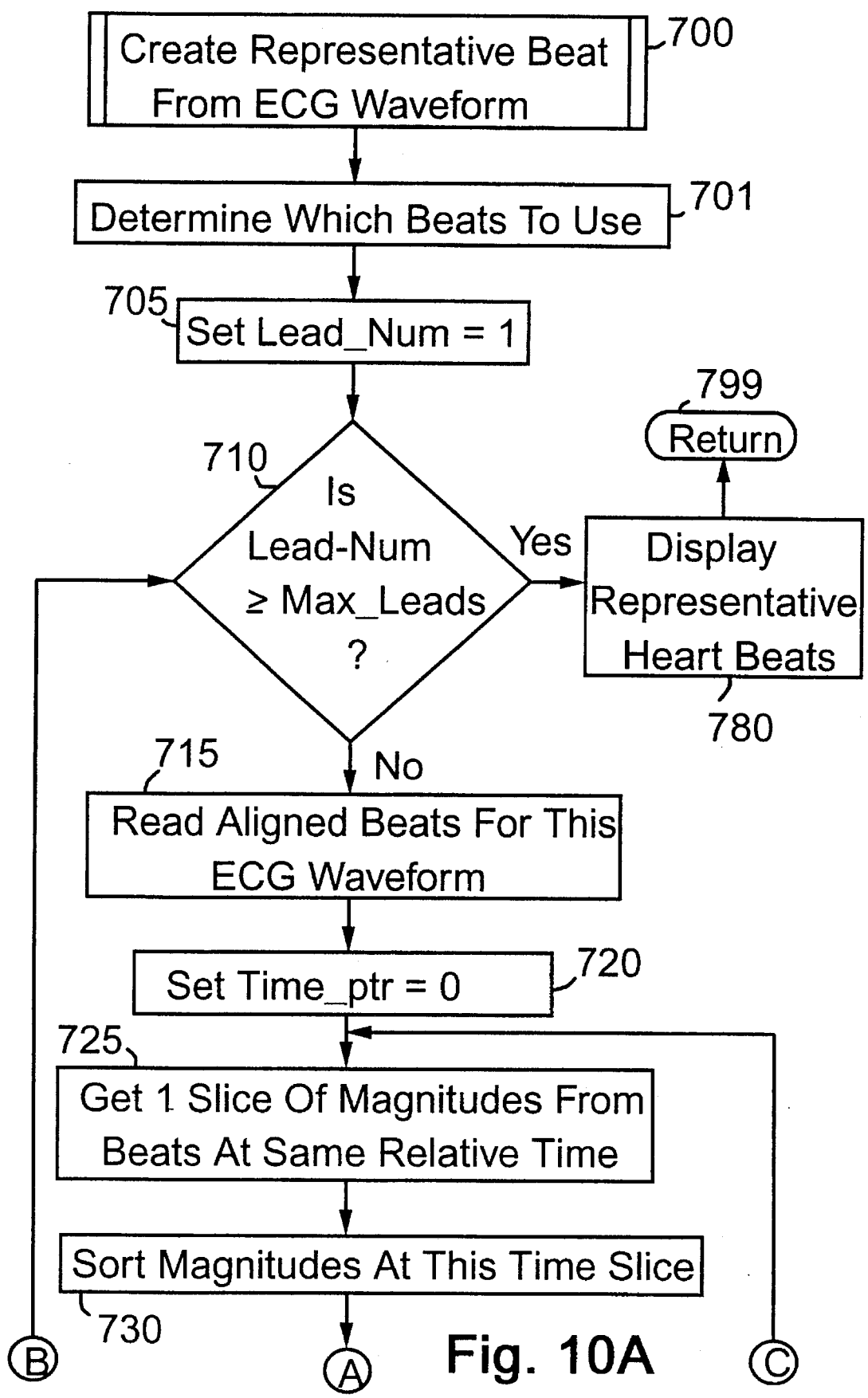
FIGS. 10A–10B show a flowchart of the operation of the representative heartbeat creation logic of the preferred embodiment of the invention.
Figure 10B:
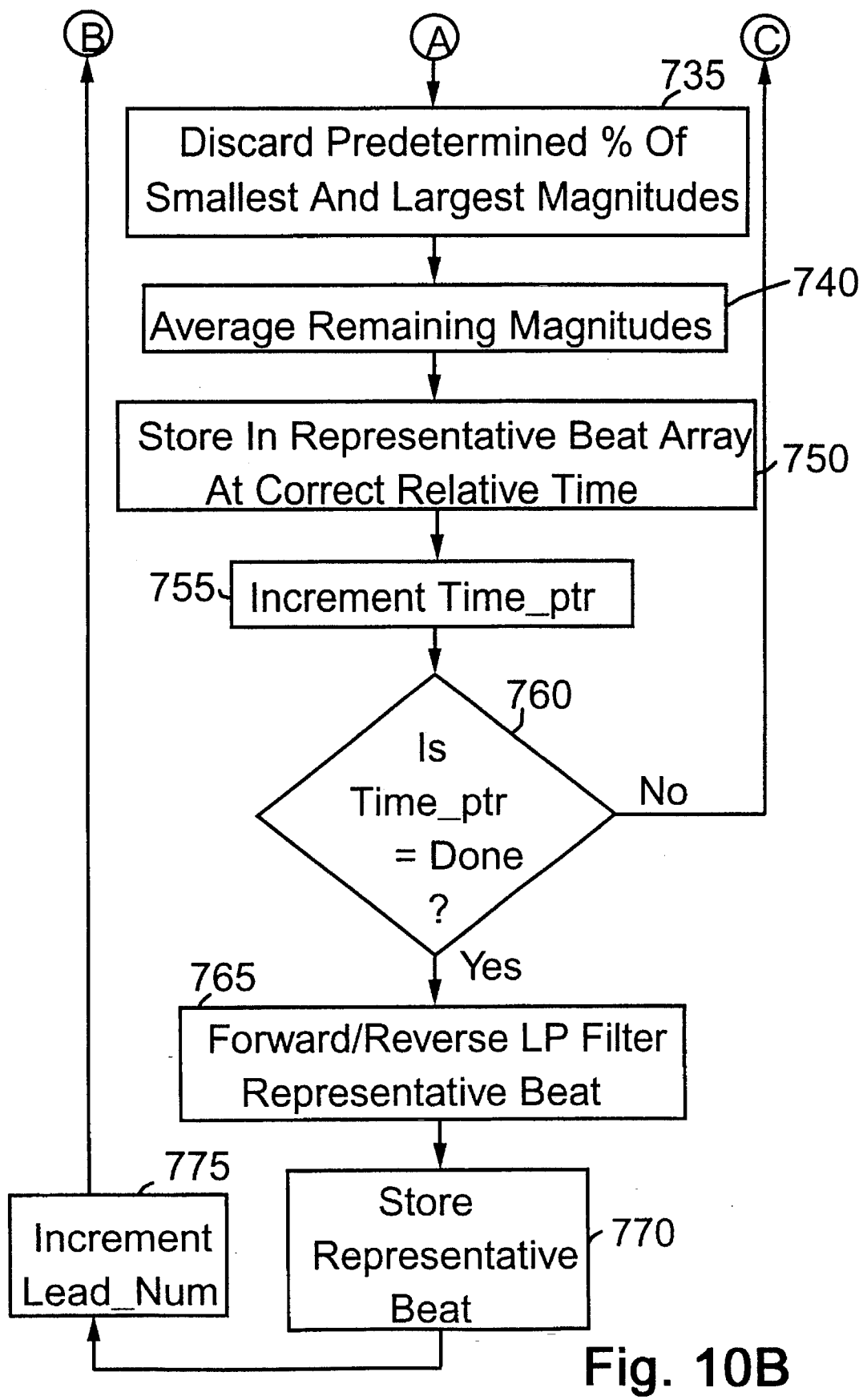

FIGS. 10A–10B show a flowchart of the operation of subroutine 700, performed by representative heartbeat creation logic 77 of computing unit 60 of the preferred embodiment of the invention. Block 701 determines which beats to use in creating the representative heartbeat. In the preferred embodiment, only "dominant" beats, aligned via the beat alignment steps discussed above, are used. If more "dominant" beats are available than the number needed to construct a representative heartbeat, those with the most similar morphology are used. For example, if two or more dominant templates were created in classification subroutine 500, only the beats that match the dominant template that contains the most beats will preferably be used. Block 705 sets a counter which keeps track of which ECG waveform the representative heartbeat is being created for to one.

Block 710 checks to see if the lead number counter is greater than or equal to the maximum number of ECG waveforms. If not, block 715 reads the aligned "dominant" beats for this ECG waveform. Block 720 sets a time pointer to zero.

Block 725 gets a time slice of data for each aligned beat at the instance of time identified by the time pointer. In the preferred embodiment, this data is the magnitude of each of the aligned dominant heartbeats at this moment of time. Block 730 sorts the magnitudes for this slice of time from smallest to largest. Block 735 discards a percentage of the smallest and largest magnitudes. In a noisy environment, the beat classification subroutine may incorrectly classify beats as being dominant. These errors result in misclassified beats being incorrectly included in the aligned beats. The trimmed average done here results in a robust and accurate representative heartbeat even in the presence of misclassified beats and high noise present on dominant beats. In the preferred embodiment, 33% of the smallest magnitudes and 33% of the largest magnitudes are discarded, although other values could be used. Block 740 averages the remaining magnitudes for this time slice. Block 750 stores the average magnitude for this time slice in a representative beat array in storage 69 of computing unit 60. Block 755 increments the time pointer to the next slice of time, and block 760 checks to see if the time pointer has reached its maximum value. If not, flow of control loops back to block 725 to determine the average magnitude of the other slices of time to complete the representative heartbeat array. FIG. 17 shows exemplary aligned beats being time sliced using the process described above.

When block 760 is answered affirmatively, block 765 forward and reverse filters the representative heartbeat stored in the representative heartbeat array, and stores the result back into the array in block 770. An alternate embodiment has been contemplated where this step is skipped. Block 775 increments the ECG waveform counter, and flow of control loops back to block 710 to create a representative heartbeat for each of the other ECG waveforms. Once block 710 determines that representative heartbeats have been created and stored for each of the ECG waveforms, block 780 displays the representative heartbeats on display 66 of computing unit 60. An exemplary display of a representative heartbeat is shown in FIG. 18. The subroutine returns in block 799 to block 800. of FIG. 5.

VII. Measurements

Figure 11A:
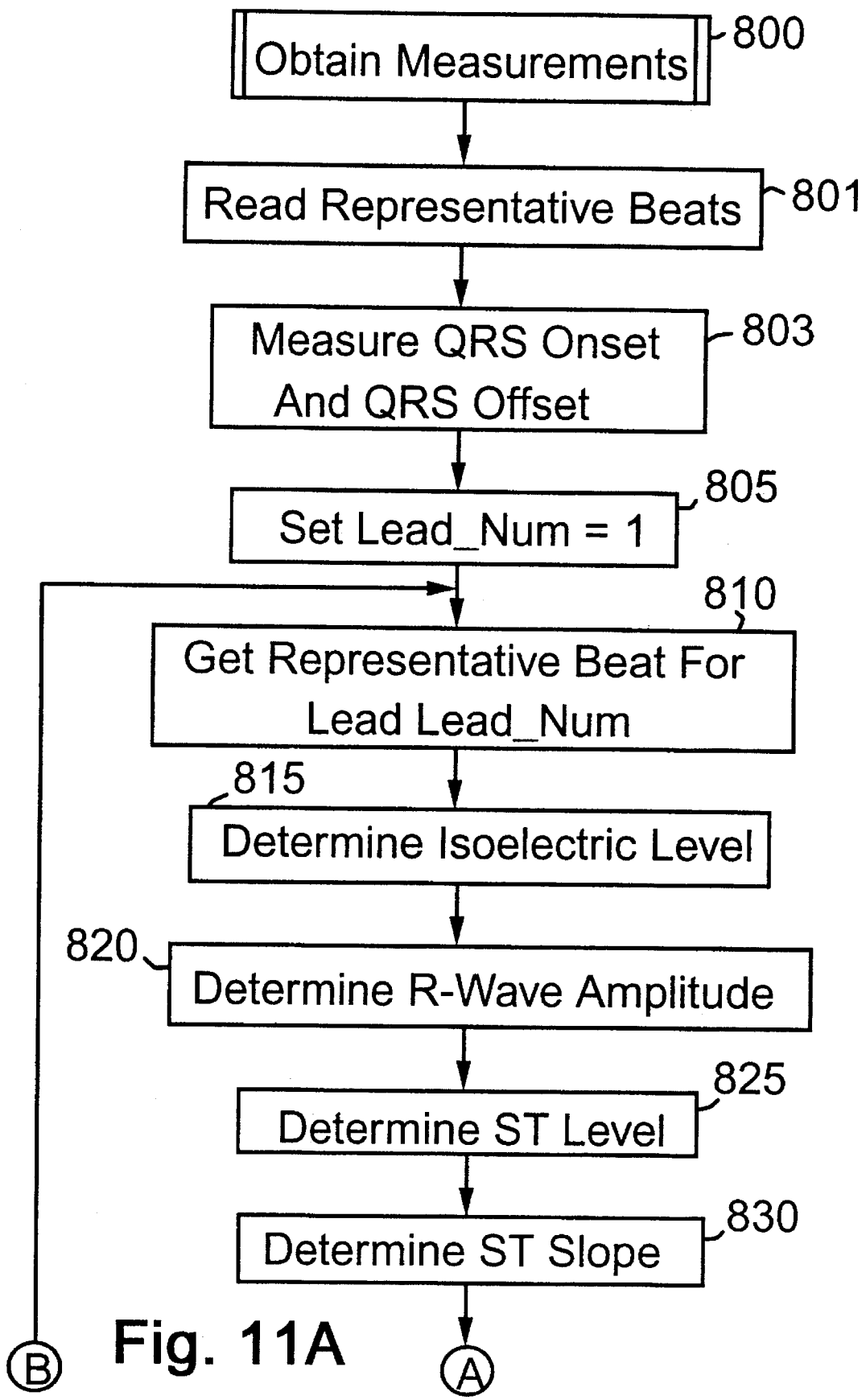
FIGS. 11A–11B show a flowchart of the operation of the measurements logic of the preferred embodiment of the invention.
Figure 11B:
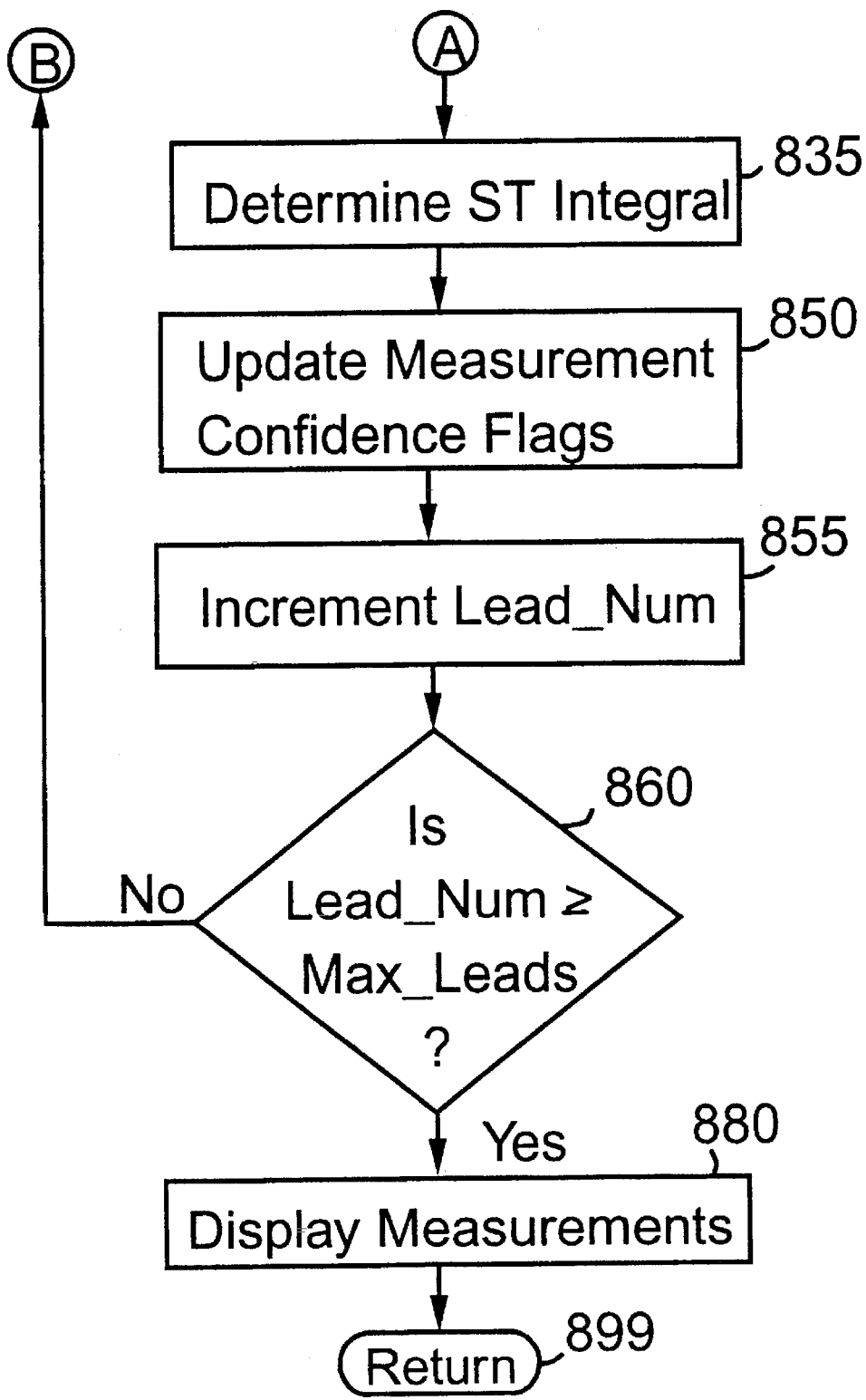

FIGS. 11A–11B shows a flowchart of the operation of subroutine 800, performed by measurements logic 78 of computing unit 60 of the preferred embodiment of the invention. Block 801 obtains the representative heartbeats for each of the ECG waveforms. In the preferred embodiment, this is done by reading the representative heartbeat array stored in step 770 of FIG. 10B. Alternatively, representative heartbeats created using a different method, including conventionally known methods for creating representative heartbeats, could be used.

Block 803 measures the earliest QRS onset and the latest QRS offset of all of the representative heartbeats obtained in block 801. These values are used for many of the measurements that will be made for these representative heartbeats, as will soon be discussed. Block 805 sets a counter that keeps track of the ECG waveform for which the representative heartbeat is being measured. Block 810 gets the representative heartbeat for this ECG waveform. Block 815 determines the isoelectric level of the representative heartbeat. In the preferred embodiment, this is the average level of the 16 msec of data prior to the earliest QRS onset. Block 820 determines the R wave amplitude for this representative heartbeat. In the preferred embodiment, this is the maximum positive value between the earliest QRS onset and the latest QRS offset, with an adjustment made to correct for elevated ST segments at the latest QRS offset, if the "T" wave is so large that it impacts the determination of the R wave amplitude.

Block 825 determines the ST level. In the preferred embodiment, this is the average of 10 msec around the user-determined ST measurement point of the representative heartbeat. Block 830 determines the ST slope. In the preferred embodiment, this is determined by using a best line fit between the latest QRS offset and the ST measurement point of the representative heartbeat. Block 835 determines the ST integral. In the preferred embodiment, this is determined by computing the sum of the negative area between the latest QRS offset and the ST measurement point of the representative heartbeat.

Block 850 updates a measurement confidence flag for each measurement taken. In the preferred embodiment, historical information and physiologic limits are used to set these measurement flags to either a "low" or "high" confidence. These confidence flags can be displayed to a user in a variety of ways, including the term "low" or "high" displayed next to a measurement, changing the color of the measurement on the display (e.g., green means high, red means low), etc. A "low" confidence flag would indicate to the cardiologist or other medical professional that a measurement is not physiologic or has changed in a non-physiologic manner and should be manually reviewed for correctness. Block 855 increments the ECG waveform counter. Block 860 checks to see if the ECG waveform counter exceeds the maximum number of ECG waveforms. If not, flow of control loops back to block 810 to repeat the process for the other ECG waveforms. If so, block 880 displays the measurements on display 66 of computing unit 60 (FIG. 2). An exemplary display of these measurements, displayed along with the representative heartbeat, is shown in FIG. 19. A cardiologist looking at the representative heartbeat and the measurements shown in FIG. 19 would see that there is a depressed ST segment, indicating that the patient undergoing a stress test has coronary artery disease. The subroutine returns in block 899 to block 210 of FIG. 5.

What is claimed is:

1. A method of creating information about a representative heartbeat from an ECG waveform, said method comprising the steps of:

detecting a plurality of heartbeats in said ECG waveform;

classifying said plurality of heartbeats as dominant heartbeats and non-dominant heartbeats;

aligning said dominant heartbeats to create aligned dominant heartbeats;

creating a representative heartbeat from said plurality of aligned dominant heartbeats, said creating step further comprising the steps of:

time slicing through said plurality of aligned dominant heartbeats;

responsive to said time slicing step, determining the magnitudes of each of said plurality of aligned dominant heartbeats at a first slice of time, thereby creating first magnitudes;

sorting the first magnitudes from smallest first magnitude to largest first magnitude, thereby creating sorted first magnitudes;

first discarding a first percentage of the smallest first magnitudes;

second discarding a second percentage of the largest first magnitudes, wherein said first magnitudes remaining after said first discarding step and said second discarding step are remaining first magnitudes;

averaging said remaining first magnitudes, thereby creating an average first magnitude; and storing said average first magnitude.

2. The method of claim 1, further comprising the steps of:

responsive to said time slicing step, storing the magnitudes of each of said plurality of aligned dominant heartbeats at a second slice of time, thereby creating second magnitudes;

sorting the second magnitudes from smallest second magnitude to largest second magnitude, thereby creating sorted second magnitudes;

third discarding said first percentage of the smallest second magnitudes;

fourth discarding said second percentage of the largest second magnitudes, wherein said second magnitudes remaining after said third discarding step and said fourth discarding step are remaining second magnitudes;

averaging said remaining second magnitudes, thereby creating an average second magnitude; and storing said average second magnitude.

3. The method of claim 2, further comprising the steps of:

responsive to said time slicing step, storing the magnitudes of each of said plurality of aligned dominant heartbeats at 3rd-N slices of time, thereby creating 3rd-N magnitudes;

sorting the 3rd-N magnitudes from smallest 3rd-N magnitudes to largest 3rd-N magnitudes, thereby creating sorted 3rd-N magnitudes;

fifth discarding said first percentage of each of the smallest 3rd-N magnitudes;

sixth discarding said second percentage of each of the largest 3rd-N magnitudes, wherein said 3rd-N magnitudes remaining after said fifth discarding step and said sixth discarding step are remaining 3rd-N magnitudes;

averaging said remaining 3rd-N magnitudes, thereby creating average 3rd-N magnitudes; and storing said average 3rd-N magnitudes.

4. The method of claim 3, further comprising the steps of:

generating said representative heartbeat from said first average magnitude, said second average magnitude, and said 3rd-N average magnitudes; and displaying said representative heartbeat.

5. The method of claim 4, wherein said first discarding step discards 33% of the smallest magnitudes at said first, second, and 3rd-N slices of time.

6. The method of claim 5, wherein said second discarding step discards 33% of the largest magnitudes at said first, second, and 3rd-N slices of time.

7. The method of claim 6, further comprising the step of:

creating a plurality of representative heartbeats corresponding to a plurality of ECG waveforms.

8. The method of claim 1, further comprising the step of:

obtaining measurements for said representative heartbeat.

9. The method of claim 8, further comprising the step of:

displaying said representative heartbeat and said measurements for said representative heartbeat.

10. The method of claim 9, further comprising the steps of:

calculating a rate of said plurality of heartbeats; and displaying said representative heartbeat and said rate of said plurality of heartbeats.

11. The method of claim 1, further comprising the step of:

displaying said representative heartbeat.

12. The method of claim 1, wherein said step of aligning said dominant heartbeats to create aligned dominant heartbeats further comprises the steps of:

creating an alignment template;

sliding a first heartbeat from said plurality of dominant heartbeats across said alignment template;

while performing said sliding step, computing an area difference between said first heartbeat and said alignment template;

determining a first position of said first heartbeat when said area difference is minimum; and storing said first position of said first heartbeat as a best aligned position.

13. The method of claim 12, further comprising the step of:

repeating the creating, sliding, computing, determining and storing steps for the other heartbeats in said plurality of dominant heartbeats, thereby creating said aligned heartbeats.

14. The method of claim 13, further comprising the steps of:

selecting a subset of said plurality of ECG waveforms that have optimal noise characteristics; and selecting said plurality of dominant heartbeats from one of said subset of said plurality of ECG waveforms that have optimal noise characteristics.

15. The method of claim 13, further comprising the steps of:

selecting a subset of said plurality of ECG waveforms that have optimal noise characteristics;

determining a plurality of median alignment times for said subset of said plurality of ECG waveforms; and correcting said aligned heartbeats with said plurality of median alignment times.

16. A medical device for creating information about a representative heartbeat from an ECG waveform, said medical device comprising:

detection logic for detecting a plurality of heartbeats in said ECG waveform;

classification logic for classifying said plurality of heartbeats as dominant heartbeats and non-dominant heartbeats;

alignment logic for aligning said dominant heartbeats to create aligned dominant heartbeats;

representative heartbeat logic for creating a representative heartbeat from said plurality of aligned dominant heartbeats, said representative heartbeat logic further comprising:

means for time slicing through said plurality of aligned dominant heartbeats;

means, responsive to said time slicing means, for determining the magnitudes of each of said plurality of aligned dominant heartbeats at a first slice of time, thereby creating first magnitudes;

means for sorting the first magnitudes from smallest first magnitude to largest first magnitude, thereby creating sorted first magnitudes;

first discarding means for discarding a first percentage of the smallest first magnitudes;

second discarding means for discarding a second percentage of the largest first magnitudes, wherein said first magnitudes remaining after said first discarding means and said second discarding means are remaining first magnitudes;

means for averaging said remaining first magnitudes, thereby creating an average first magnitude; and means for storing said average first magnitude.

17. The medical device of claim 16, further comprising:

responsive to said time slicing means, means for storing the magnitudes of each of said plurality of aligned dominant heartbeats at a second slice of time, thereby creating second magnitudes;

means for sorting the second magnitudes from smallest second magnitude to largest second magnitude, thereby creating sorted second magnitudes;

third discarding means for discarding said first percentage of the smallest second magnitudes;

fourth discarding means for discarding said second percentage of the largest second magnitudes, wherein said second magnitudes remaining after said third discarding means and said fourth discarding means are remaining second magnitudes;

means for averaging said remaining second magnitudes, thereby creating an average second magnitude; and means for storing said average second magnitude.

18. The medical device of claim 17, further comprising:

responsive to said time slicing means, means for storing the magnitudes of each of said plurality of aligned dominant heartbeats at 3rd-N slices of time, thereby creating 3rd-N magnitudes;

means for sorting the 3rd-N magnitudes from smallest 3rd-N magnitudes to largest 3rd-N magnitudes, thereby creating sorted 3rd-N magnitudes;

fifth discarding means for discarding said first percentage of each of the smallest 3rd-N magnitudes;

sixth discarding means for discarding said second percentage of each of the largest 3rd-N magnitudes, wherein said 3rd-N magnitudes remaining after said fifth discarding means and said sixth discarding means are remaining 3rd-N magnitudes;

averaging said remaining 3rd-N magnitudes, thereby creating average 3rd-N magnitudes; and storing said average 3rd-N magnitudes.

19. The medical device of claim 18, further comprising:

means for generating said representative heartbeat from said first average magnitude, said second average magnitude, and said 3rd-N average magnitudes; and a display for displaying said representative heartbeat.

20. The medical device of claim 18, further comprising:

means for generating said representative heartbeat from said first average magnitude, said second average magnitude, and said 3rd-N average magnitudes; and a printer for printing said representative heartbeat.

21. The medical device of claim 18, wherein said first discarding means discards 33% of the smallest magnitudes at said first, second, and 3rd-N slices of time.

22. The medical device of claim 21, wherein said second discarding means discards 33% of the largest magnitudes at said first, second, and 3rd-N slices of time.

23. The medical device of claim 22, further comprising:

means for creating a plurality of representative heartbeats corresponding to a plurality of ECG waveforms.

24. The medical device of claim 18, further comprising:

measurement logic for obtaining measurements for said representative heartbeat.

25. The medical device of claim 24, further comprising:

a display for displaying said representative heartbeat.

26. The medical device of claim 24, further comprising:

a display for displaying said representative heartbeat and said measurements for said representative heartbeat.

27. The medical device of claim 24, further comprising:

calculation logic for calculating a rate of said plurality of heartbeats; and a display for displaying said representative heartbeat and said rate of said plurality of heartbeats.

28. The medical device of claim 16, wherein said means for aligning said dominant heartbeats to create aligned dominant heartbeats further comprises:

means for creating an alignment template;

means for sliding a first heartbeat from said plurality of dominant heartbeats across said alignment template;

while performing said sliding means, means for computing an area difference between said first heartbeat and said alignment template;

means for determining a first position of said first heartbeat when said area difference is minimum; and means for storing said first position of said first heartbeat as a best aligned position.

29. The medical device of claim 28, further comprising:

means for repeating the creating, sliding, computing, determining and storing means for the other heartbeats in said plurality of dominant heartbeats, thereby creating said aligned heartbeats.

30. The medical device of claim 29, further comprising:

means for selecting a subset of said plurality of ECG waveforms that have optimal noise characteristics; and means for selecting said plurality of dominant heartbeats from one of said subset of said plurality of ECG waveforms that have optimal noise characteristics.

31. The medical device of claim 29, further comprising:

means for selecting a subset of said plurality of ECG waveforms that have optimal noise characteristics;

means for determining a plurality of median alignment times for said subset of said plurality of ECG waveforms; and means for correcting said aligned heartbeats with said plurality of median alignment times.

\* \* \* \* \*